(12) United States Patent
Still et al.

(10) Patent No.: US 11,878,330 B2
(45) Date of Patent: Jan. 23, 2024

(54) AIR/WATER CHANNEL PRE-CLEANING ADAPTER

(71) Applicant: United States Endoscopy Group, Inc., Mentor, OH (US)

(72) Inventors: Raphael Still, Richmond Heights, OH (US); Christopher J. Kaye, Middleburg Heights, OH (US); Gary Mann, Painesville, OH (US); Joseph Mrva, Kirtland, OH (US); Matt Carroll, Painesville, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 0 days.

(21) Appl. No.: 16/507,979

(22) Filed: Jul. 10, 2019

(65) Prior Publication Data

US 2020/0016637 A1  Jan. 16, 2020

Related U.S. Application Data

(60) Provisional application No. 62/696,258, filed on Jul. 10, 2018.

(51) Int. Cl.
| | | |
|---|---|---|
| *B08B 9/032* | (2006.01) | |
| *A61B 90/70* | (2016.01) | |
| *A61B 1/00* | (2006.01) | |
| *A61B 1/12* | (2006.01) | |

(52) U.S. Cl.
CPC ........ *B08B 9/0325* (2013.01); *A61B 1/00059* (2013.01); *A61B 1/00103* (2013.01); *A61B 1/125* (2013.01); *A61B 90/70* (2016.02); *A61B 2090/701* (2016.02); *B08B 2209/032* (2013.01)

(58) Field of Classification Search
CPC ... A61B 90/70; A61B 1/125; A61B 2090/701; A61B 1/015; A61B 1/00068
See application file for complete search history.

(56) References Cited

U.S. PATENT DOCUMENTS

| | | | |
|---|---|---|---|
| 4,579,598 A | 4/1986 | Sasa et al. | |
| 5,027,791 A * | 7/1991 | Takahashi | A61B 1/126 |
| | | | 600/158 |
| 5,070,829 A | 12/1991 | Guntly et al. | |
| 6,286,179 B1 | 9/2001 | Byrne | |

(Continued)

FOREIGN PATENT DOCUMENTS

| | | |
|---|---|---|
| EP | 0106310 A2 | 4/1984 |
| EP | 1762172 A2 | 3/2007 |

(Continued)

OTHER PUBLICATIONS

International Search Report and Written Opinion from PCT/US/2019/041225 dated Oct. 24, 2019.

*Primary Examiner* — Spencer E. Bell
(74) *Attorney, Agent, or Firm* — Calfee, Halter & Griswold LLP

(57) ABSTRACT

A device and assembly for a cleaning adapter to be placed in an air/water port of an endoscopic device is described. The device can have a button to control a valve stem with openings to permit the control of air and water flow, depending on the position of the cleaning adapter, which a user controls. A method and system are also described. A tag is also described, instructing the users of the proper use of the device.

25 Claims, 27 Drawing Sheets

(56) References Cited

U.S. PATENT DOCUMENTS

| | | | |
|---|---|---|---|
| 6,631,744 B1 | 10/2003 | Gerhart et al. | |
| 8,114,221 B2 | 2/2012 | Labib et al. | |
| 9,408,523 B2 | 8/2016 | Grudo et al. | |
| 2006/0100485 A1* | 5/2006 | Arai | A61B 1/015 600/159 |
| 2006/0135851 A1* | 6/2006 | Yamazaki | A61B 1/00137 600/156 |
| 2016/0143516 A1 | 5/2016 | Xu et al. | |
| 2017/0087263 A1* | 3/2017 | Sato | B08B 3/08 |
| 2018/0325358 A1* | 11/2018 | Hirayama | A61B 1/015 |

FOREIGN PATENT DOCUMENTS

| | | | |
|---|---|---|---|
| JP | S58010030 A | 1/1983 | |
| JP | S59069021 A | 4/1984 | |
| JP | H067701 U | 2/1994 | |
| WO | 2012075131 A1 | 6/2012 | |
| WO | 2014087745 A1 | 6/2014 | |
| WO | 2015080694 A1 | 6/2015 | |
| WO | 2017082204 A1 | 5/2017 | |
| WO | WO-2019226307 A1 * | 11/2019 | A61B 1/00055 |

* cited by examiner

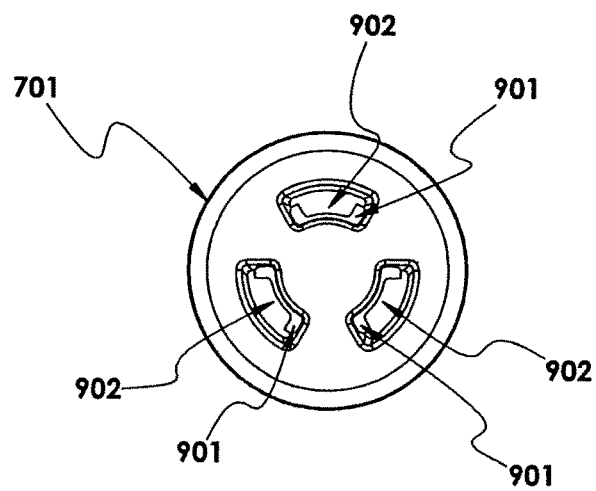
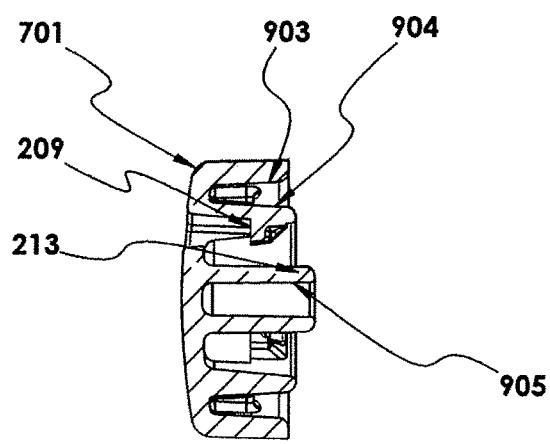
FIG. 9A
FIG. 9B
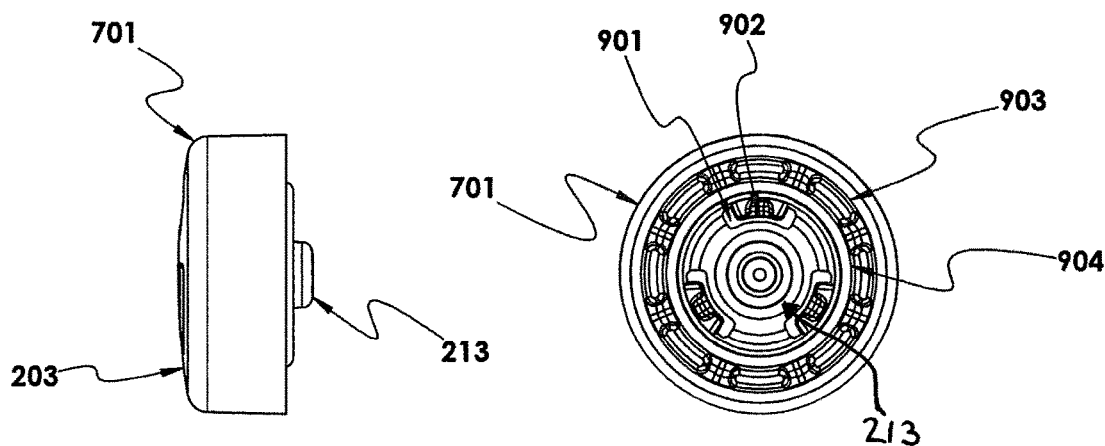
FIG. 9C
FIG. 9D

AIR/WATER CHANNEL PRE-CLEANING ADAPTER

CROSS-REFERENCE TO RELATED APPLICATIONS

The present application claims benefits and priority to U.S. Provisional Patent Application No. 62/696,258, filed on Jul. 10, 2018, the entire disclosures of which are incorporated herein by reference.

FIELD OF THE INVENTION

The various embodiments relate to an air/water channel pre-cleaning adapter for an endoscope, that can be used in the pre-cleaning of existing endoscopes and that is disposable. The adapter of the various embodiments can have a button that is depressed by the user to switch between air flow and water flow, or it can have a switch for the same purpose. The adapter can have a valve stem attached to a base, and the valve stem moves up and down in response to the activation of the valve by depressing the button.

BACKGROUND INFORMATION

FIG. 1A illustrates an endoscope device 100 having an air channel 101 and a water channel 102 through which air and water, respectively, can be flushed from the air/water source to the distal end of the endoscope. An endoscope typically also has an air/water cylinder 103, into which an air/water valve 112 is inserted. An air/water valve (FIG. 1B) or other valves can be inserted into the cylinder 103, as well. A typical endoscope also has an air channel 101, a water channel 102, and an air/water channel 104 extending distally where the distal ends of the air channel 101 and water channel 102 meet. The air channel provides air to the air/water channel; similarly, the water channel provides water to the air/water channel. FIG. 1B illustrates the top surface of a button 105 on a valve in FIG. 1A, inserted into cylinder 103, and the opening 110 in the top surface is illustrated. When the valve button 105 is depressed downward, water is flushed through the channel(s). When the valve is in an upward position and the hole 110 is not covered, as illustrated in FIG. 1B, air flows through the air channel from the air source into the opening 108 and out hole 110 in the air/water valve. The user may then direct air to travel from the air/water valve to the distal portion of the endoscope by covering the hole 110 on the air/water valve with a finger, while the valve is in the upward, non-depressed position. This prevents air from entering 108, and causes air to flow through the air/water channel to the distal end of the endoscope. Air/water valves are not for use during pre-cleaning or cleaning.

After use, air and water are flushed through the channels, typically to pre-clean the endoscope prior to it undergoing a high-level disinfection. A water bottle connector can be used to connect a water bottle to supply the water for the water channel. In addition, a water bottle connector may include an air tube for air to flow through. Existing air/water cleaning adapter valves 113 in the prior art do not have an opening in the top of the button of the valve. FIG. 1C illustrates a typical air/water channel cleaning adapter valve 113 in the existing art. The typical prior art adapter valve has a metal stem 202, and a button 114, as well as a tag 206 with warning information to not use during medical procedures, connected by a connecting element 207 to the adapter valve 113. The metal stem 202 has an opening 301 that connects to a central bore in the stem 202 to permit air to flow. The metal stem 202 also has an opening 302 that passes all the way through the stem and is also connected to the central bore of the stem, to permit water to flow through. The location of openings 301 and 302 relative to the channels in the endoscope depends on the position of the air/water channel cleaning adapter valve. When the button on the valve is depressed, the valve is "on," aligning the opening 302 with the water channel, and thereby fluidly connects the water channel to the air/water channel, to flush it with water.

When the button is in an upward position and not depressed, the hole is aligned with the air channel, and thereby fluidly connects the air channel to the air/water channel in the endoscope, and the air flow pushes out any remaining water. This permits air to flow through the valve and into the air/water channel.

The button 114 of the valve does not have an opening for air to exit the channel because, as the cleaning adapter valve is only to be used when the endoscope is being cleaned, there is no risk of insufflating an excess volume of air through the endoscope and into a patient. Both air and water are intended to be flushed through the channels for a longer duration of time when pre-cleaning the endoscope, to flush debris from the channels, so there is no need to have an "off" position where no water or air flows through the entire length of the endoscope channel(s).

While an endoscope that is known in the art is depicted in FIG. 1A, gastroscopes, colonoscopes, duodenoscopes, or other endoscopes may have similar air and water channels, and air/water valves. In a typical endoscope, if an air/water channel cleaning adapter valve is not being used during pre-cleaning, then a user must cover the opening of the typical air/water valve with a thumb or other finger the entire time air is to flow through the air channel to clean the endoscope. Existing air/water channel cleaning adapter valves present problems. First, because a user must press down the entire time water is to be flushed through an endoscope, the prior art air/water channel cleaning valve adapters cause fatigue while water is being flushed through the endoscope. Next, because they are reusable, they are often not cleaned properly in between uses. The many components such as the spring holding the button in an upward default position make cleaning more difficult and increase the chances of the adapter breaking. They are also easy to lose. Thus, there is a need for an air/water channel cleaning adapter that does not cause the same fatigue to a user's hand as prior art air/water channel cleaning adapter valves, that is for single-use, and that can be used during pre-cleaning. Exemplary embodiments of the disposable air/water channel pre-cleaning adapter described below and illustrated in the remaining figures can be used to replace current re-processable air/water channel cleaning adapters and can be used to reduce and/or eliminate this fatigue. The disposable air/water channel pre-cleaning adapter according to the exemplary embodiments described below can be placed in a typical air/water cylinder 103 and provides a control mechanism for permitting air and water to flow through the channels. The exemplary embodiments described below eliminate the need for a spring, and also eliminates the need for a user to continuously hold the pre-cleaning adapter button down when flushing water through the device.

SUMMARY OF THE INVENTION

One or more embodiments of a device for placement in an air/water cylinder of an endoscope to control the flow of air and water can have a base; a button; a valve stem; a channel positioned longitudinally through the valve stem, having an open proximal end and a closed distal end. The device can have a first opening through a wall of the valve stem to the channel and a second opening through a wall of the valve stem to the channel. The device further can have the button connected at a proximal end of the valve stem. A proximal end of the valve stem extends through the base and is connected to a distal end of the button. The device can be configured to move between a first position and a second position. In the first position, the button and valve stem are in a proximal position relative to the base. In the second position, the button and valve stem can be in a distal position relative to the first position.

Further, when in the first position, the first and second openings can be aligned with an air flow channel of an endoscopic device. When in the second position the first and second openings can be aligned with a water flow channel of an endoscopic device.

In the exemplary embodiments, the device can have a button that is a half-spherical shape comprised of a flexible material, or the button can be cylindrical with a substantially flat proximal surface and is further comprised of a rigid polymer.

The device can have a tag attached to the base, where the tag contains written or symbolic information for the user. The tag can be molded to the base or it can be attached to the base via an elongated element. The device can also have seals attached to the valve stem to prevent leakage of fluid. The tag can warn users not to use the device with an endoscope on patients because the device was not designed for this purpose.

One or more exemplary embodiments of the device can be a part of a system for cleaning channels of an endoscopic device having an air channel, a water channel, an air/water channel, and a water source connected to the endoscopic device. The system can have a removable valve channel adapter having the components of any of the embodiments described herein, including first and second openings in the channel of the valve stem, to fluidly connect the central channel of the valve stem with one or more air and water channels. In the exemplary embodiments described herein, the first and second openings can be aligned with the air channel when the valve stem is in a proximal position and can be aligned with the water channel when the valve stem is in a distal position.

One or more exemplary embodiments described herein can include a method of using any of the exemplary embodiments of device or system described herein, for pre-cleaning an endoscopic device. The method of pre-cleaning can comprise the steps of inserting an air/water channel cleaning adapter valve into an air-water cylinder of an endoscopic device; connecting a water source to the endoscopic device; aligning a fluid channel in a stem of the air/water channel cleaning adapter with a water channel of the endoscopic device; and flushing debris from at least one channel of the endoscopic device with water while the air/water channel cleaning adapter is in the second position. The method can also include the step of purging water and leftover debris from at least one channel of the endoscopic device by removing downward pressure from the button, thereby aligning the fluid channel with an air channel of the endoscopic device. The device described herein can be disposable.

These and aspects of the exemplary embodiments will become apparent from the following detailed description, taken in conjunction with the accompanying drawings, illustrating by way of example the principles of the various exemplary embodiments.

BRIEF DESCRIPTION OF THE DRAWINGS

In order to facilitate a fuller understanding of the exemplary embodiments, reference is now made to the appended drawings. These drawings should not be construed as limiting, but are intended to be exemplary only.

FIG. 9A depicts a top view of a button cap for an air/water channel pre-cleaning adapter in accordance with an exemplary embodiment.

FIG. 9B depicts a cross-section view of the button cap of FIG. 9A, in accordance with an exemplary embodiment.

FIG. 9C depicts a side view of the button cap of FIG. 9A, in accordance with an exemplary embodiment.

FIG. 9D depicts a bottom view of the button cap of FIG. 9A, in accordance with an exemplary embodiment.

DETAILED DESCRIPTION OF EMBODIMENTS

The following description is intended to convey a thorough understanding of the embodiments by providing various embodiments and details involving variations on the air/water channel pre-cleaning adapter switch/button valve and the connectivity of the tag. It is understood, however, that the invention is not limited to these specific embodiments and details, which are exemplary only. It is further understood that one possessing ordinary skill in the art, with respect to known devices, systems and methods, would appreciate the use of the invention for its intended purposes and benefits in any number of alternative embodiments.

Figure 2A:
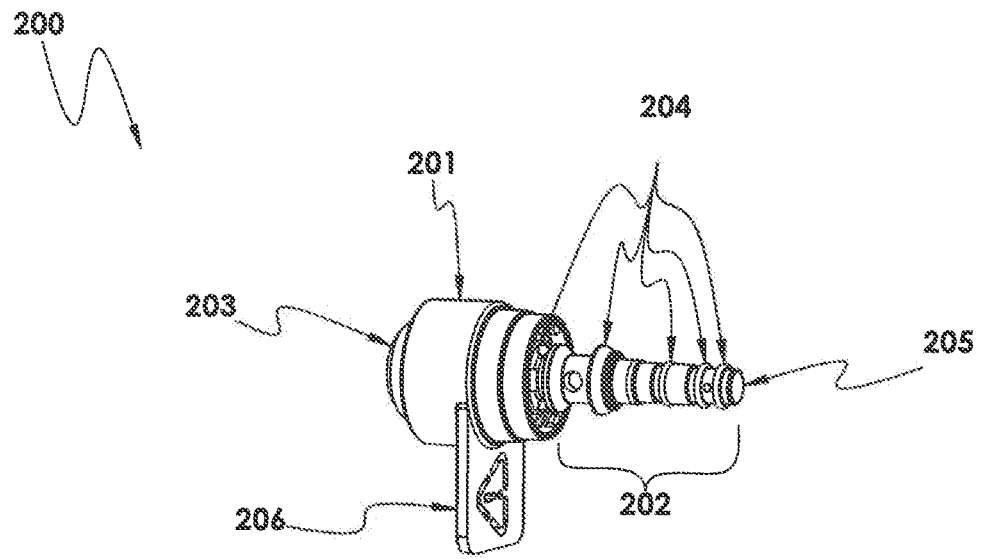
FIG. 2A depicts an air/water channel pre-cleaning adapter having a dome button with one possible tag embodiment in accordance with an exemplary embodiment.
Figure 2B:
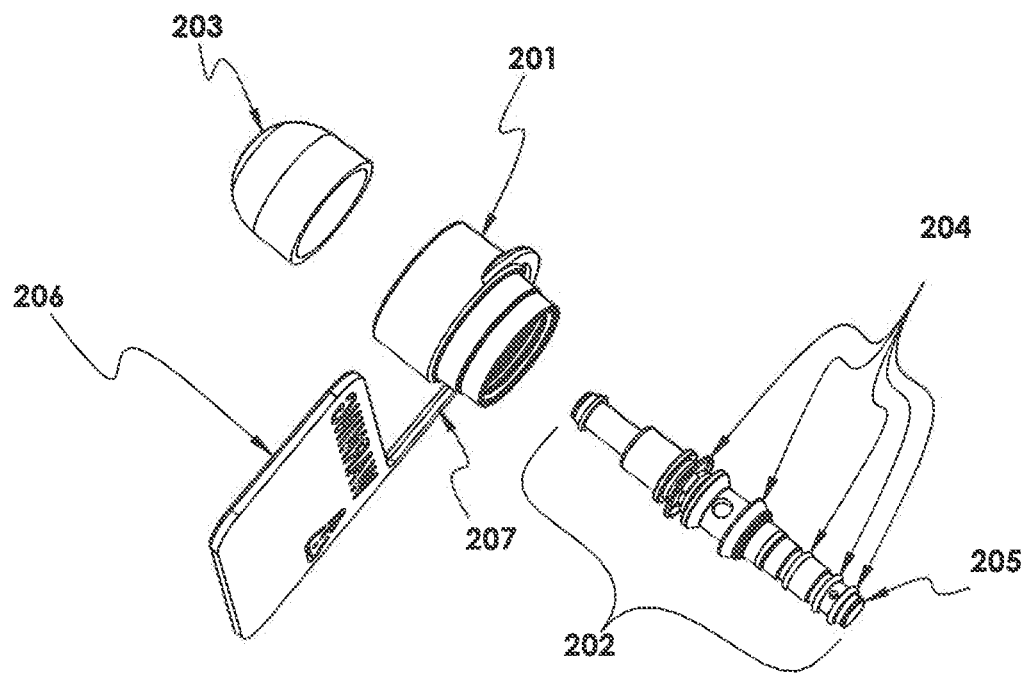
FIG. 2B depicts an exploded view of the air/water channel pre-cleaning adapter with another possible tag embodiment of FIG. 2A, in accordance with an exemplary embodiment.
Figure 2C:
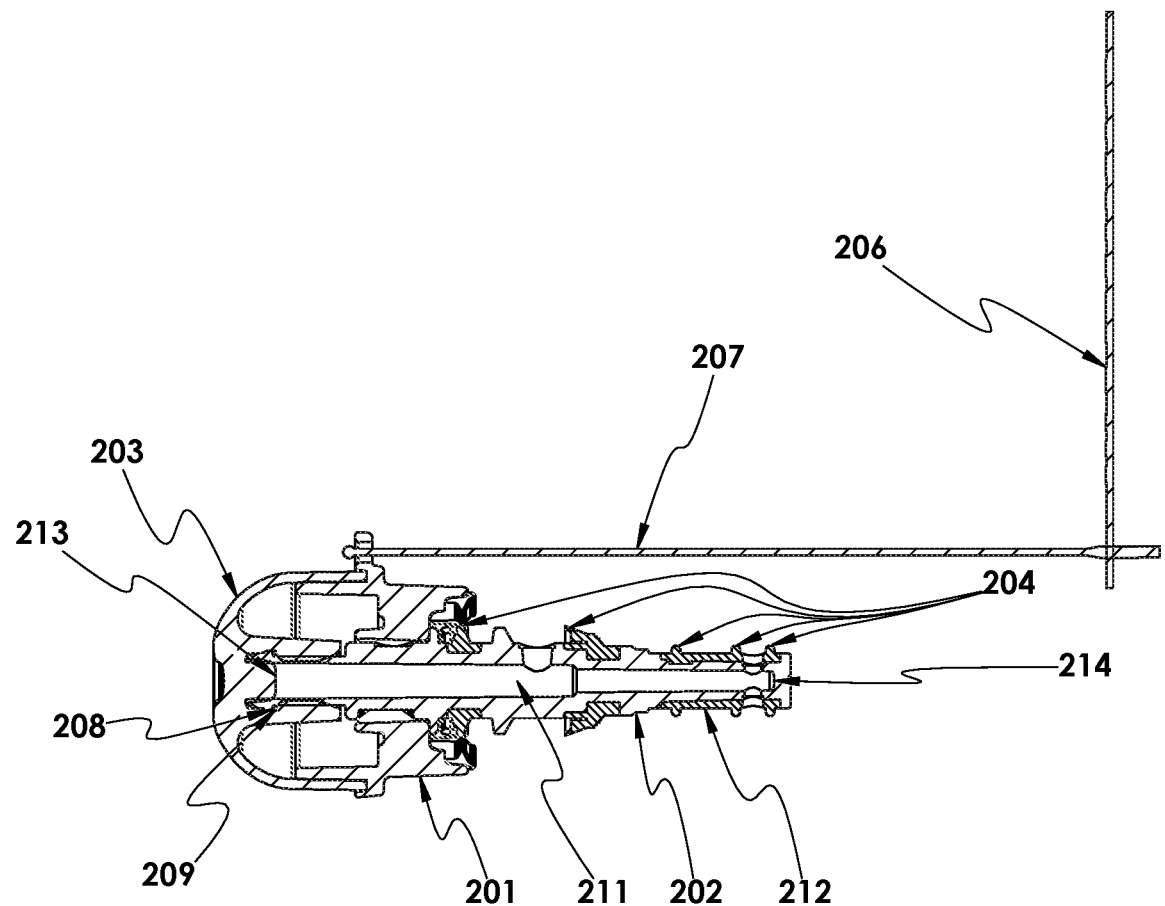
FIG. 2C depicts a cross-section view of an air/water channel pre-cleaning adapter with another possible tag embodiment of FIG. 2A, in accordance with an exemplary embodiment.

FIGS. 2A-2C illustrate a dome button embodiment of an air water pre-cleaning adapter valve 200. The air/water channel cleaning adapter can have a valve base 201, a valve stem 202 and a button 203, as shown in FIG. 2A. The valve stem can also have seals 204 that act as a piston 205. The valve stem can be a sliding element. The valve base 201 can have a tag 206 attached to it, either integrated or connected through another means. In FIG. 2A, the tag 206 is integrated into and extends outward directly from the base 201. Each component, its purpose, and relation to the other components will be described in detail herein. FIG. 2B is an exploded view of another possible form of the air/water channel pre-cleaning adapter valve in FIG. 2A. The base 201 can be molded from any number of thermoplastic or thermoset materials such as polyethylene, polypropylene, polycarbonate, or diallyl phthalate. In FIG. 2B, the tag 206 is connected to the base 201 by an extender 207. The tag can contain information for the user. The extender 207 and tag 206 can be molded as one piece integrated with the base 201. The extender can be a tether or other elongated element. The tag can have a warning label molded into it or otherwise printed or stamped on it. The stem 202 can be molded and can have gaskets (seals) 204 over-molded onto the stem. The button 203 can be a dome cap. The button can be made of any number of thermoplastic or thermoset materials such as flexible PVC, thermoplastic elastomers, or silicone.

Figure 1A:
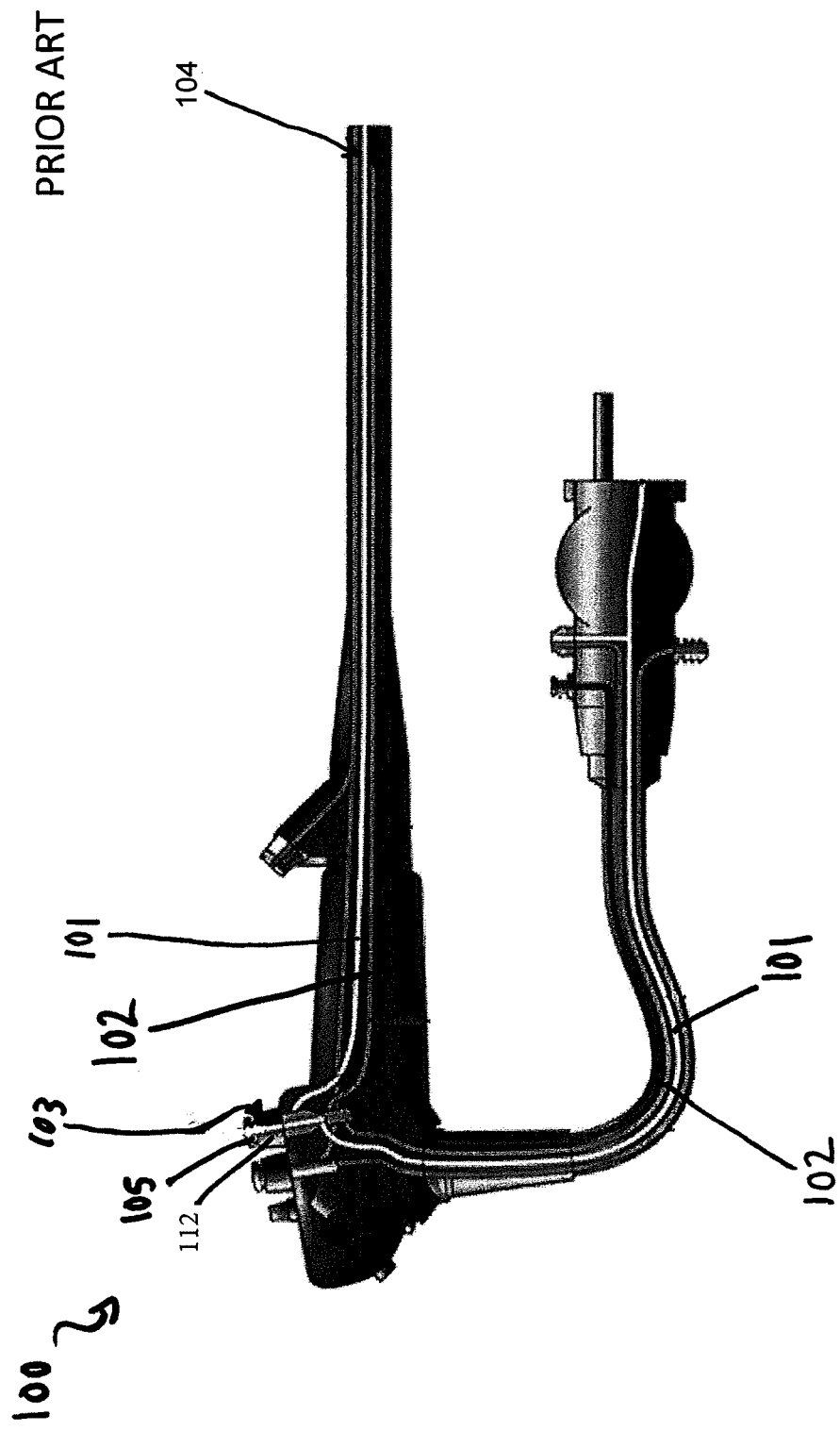
FIG. 1A depicts an endoscope as known in the prior art having an air/water valve.
Figure 1B:
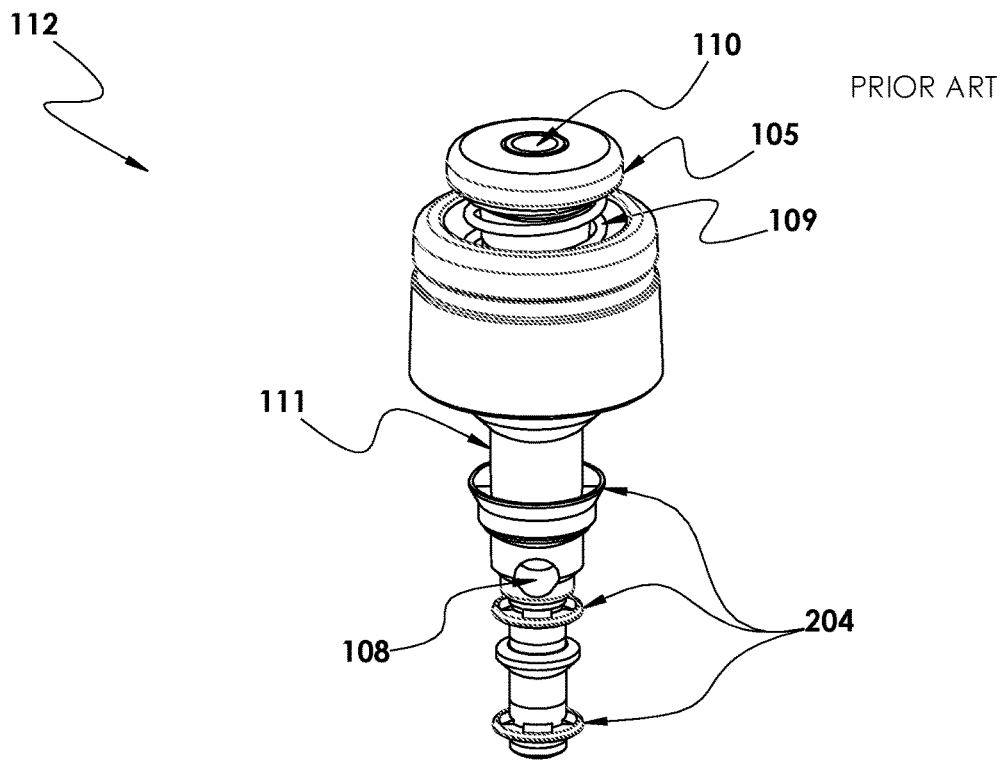
FIG. 1B depicts a prior art air/water channel valve for an endoscope for use during a medical procedure.

FIG. 2C illustrates a cross-section of the dome cap pre-cleaning adapter valve according to an exemplary embodiment. The dome cap 203 can be attached to the valve stem 202 by a lock feature molded into the valve stem 202. The lock feature can have two corresponding parts, a first lock feature component 208 can be located on the valve stem, and a second lock feature component 209 can be located on the dome cap. There can be a seal hub 213 as part of the interior of the dome cap that fits into a first end of the cylindrically shaped valve stem. The valve stem can have a cylindrical bore 211 (center channel) running longitudinally through the valve stem 202. At a first end, the cylindrical bore 211 is fit with the seal hub 213 of the dome cap. A second end 214 of the valve stem is closed. Each of the components in accordance with an exemplary embodiment is described in greater detail below, followed by schematics of a first and second position of an exemplary embodiment of an air/water channel pre-cleaning adapter valve in FIGS. 2D and 2E. In use, when the dome cap is depressed, once a user's finger is removed from the dome cap, it will rise back up to an upward position. This upward position is the position that allows air to flow through the air channel and then the air/water channel. The depressed position permits water to flow through the water channel and then through the air/water channel. The dome cap does not rely on any spring or coil to rise upward. Rather, it relies on the intrinsic properties of the material it is made of and its shape. The dome button reduces user fatigue because it is easier to depress than a button with a coil spring, and only requires a user to hold a finger down on the dome cap when the user wants air to flow through the air/water channel, unlike an existing air/water channel valve such as that in FIG. 1B which requires a user to continuously contact the button whether air or water is to flow through the air/water channel.

Figure 3A:
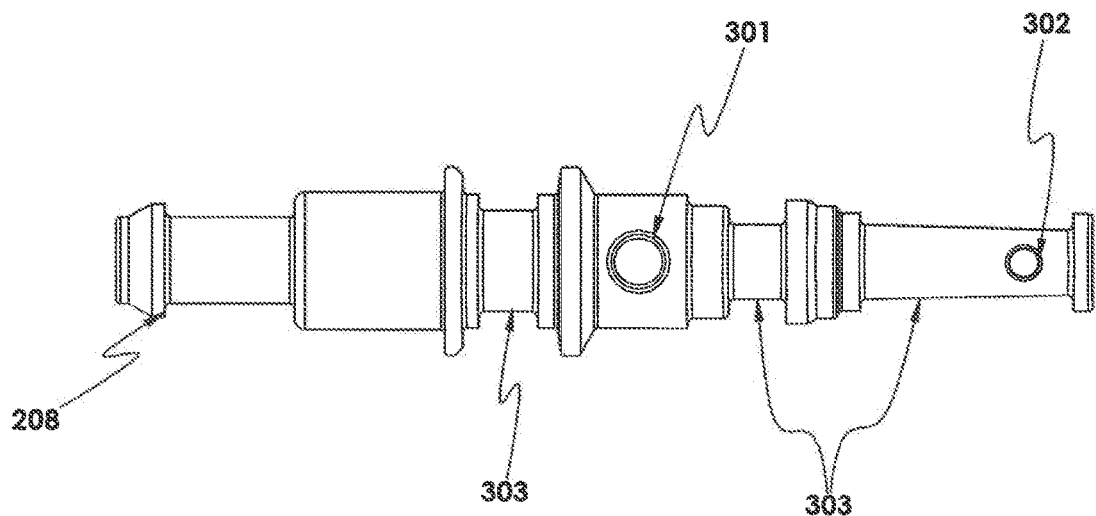
FIG. 3A depicts a valve stem of an air/water channel pre-cleaning adapter in accordance with an exemplary embodiment.
Figure 3B:
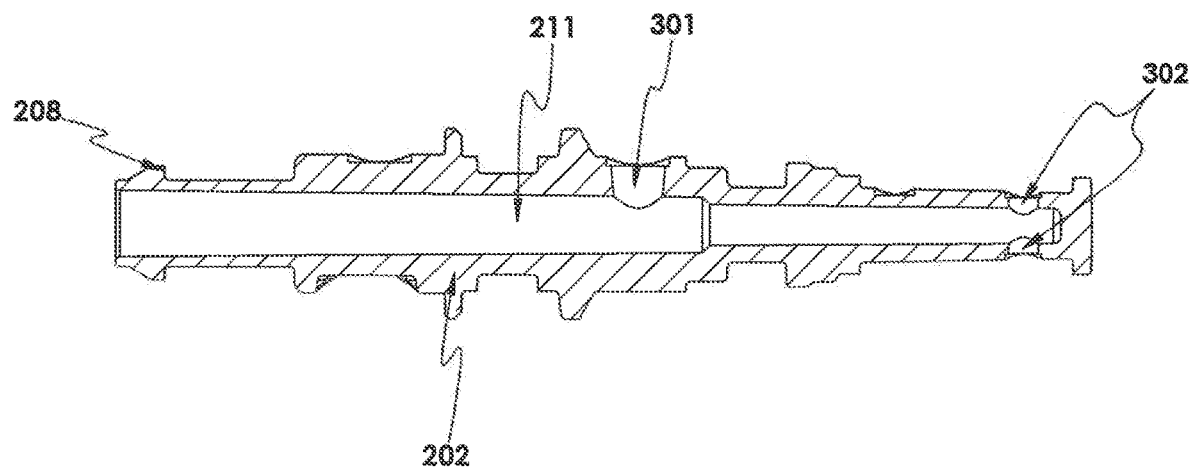
FIG. 3B depicts a cross section view of the valve stem of FIG. 3A, in accordance with an exemplary embodiment.

Additional openings 301, 302 in the valve stem 202 can be seen in FIGS. 3A and 3B. FIG. 3A illustrates the exterior surface of the valve stem 202, which has proximal side holes 301 and distal side holes 302 to allow air and/or water to flow between the distal and proximal ports in the scope cylinder. The proximal and distal holes are connected by the center channel 211 (bore) which permits air and/or water to flow between the holes 301, 302. At the proximal end of the valve stem, the lock feature components 208, 209 are illustrated as a wider diameter portion that slopes outward from proximal to distal direction, then abruptly returns to a smaller diameter. The abrupt change in diameter creates a catch for the dome cap 203 to interlock with. Once the dome cap is positioned beyond the catch, it is prevented from falling off the valve stem. Along the length of the valve stem can be grooves 303 shaped and positioned to retain sealing gaskets 204 to help the pre-cleaning adapter valve function. In the exemplary embodiment of FIGS. 2A-C, some of the gaskets can be combined into one continuous part connected by a connecting portion 212, illustrated in FIG. 2C, that can then be over-molded onto the valve stem. The connecting portion 212 can be a sleeve that fits around the circumference of the valve stem, or it can be strips of material that connect the gaskets together.

Figure 4A:
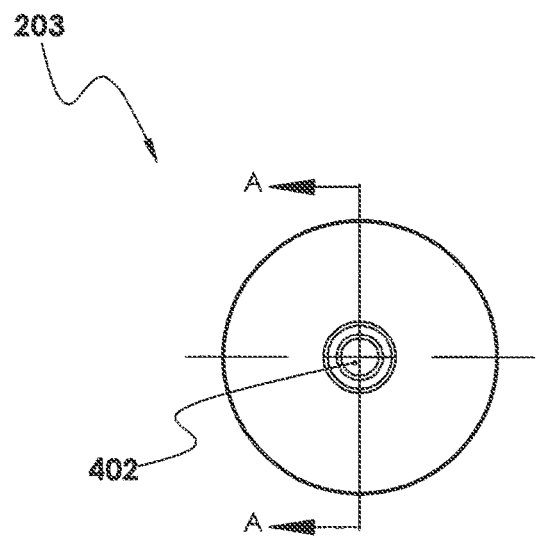
FIG. 4A depicts a top view of a dome cap for an air/water channel pre-cleaning adapter in accordance with an exemplary embodiment.
Figure 4B:
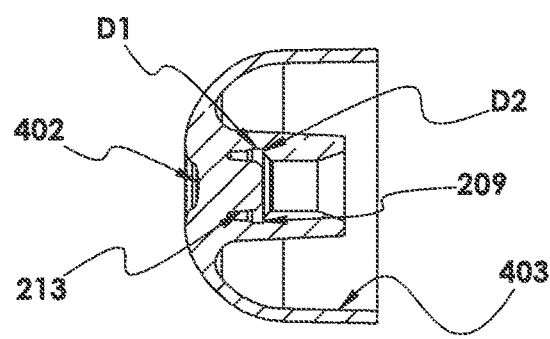
FIG. 4B depicts a cross-section view of the dome cap of FIG. 4A, in accordance with an exemplary embodiment.

FIGS. 4A-4K illustrate the dome cap 203 in greater detail. The dome cap 203 can have one of a variety of shapes and can have a recessed area 402 of one of a variety of shapes. FIG. 4A illustrates the top, exterior surface of an exemplary embodiment of a dome cap 203 having a half-spherical form, and a recessed area 402. The dome cap can have a centrally located recessed area 402 that can provide a tactile indicator to further reinforce that the user's finger is centered on the dome cap, which is where the user should press, alleviating the need to look at the dome cap. The recessed area 402 can have a circular shape, as illustrated in FIG. 4A. FIG. 4B is a cross-section view taken from lines A-A in FIG. 4A. Visible from this view, is the seal hub 213, a lock feature component 209, and an interior wall surface 403. The seal hub provides a hub to enter the proximal end of the central channel of the valve stem. The lock feature is a change in the interior contour of the dome cap where the proximal-most diameter D1 is greater than an adjacent diameter D2, located distal to D1. This change in the diameter provides a "shelf" along which the lock feature 208 of the valve stem 202 can interlock with. The interior wall surface can be of a size to provide an interference fit with the valve stem to further prevent air and/or water leakage.

Figure 4C:
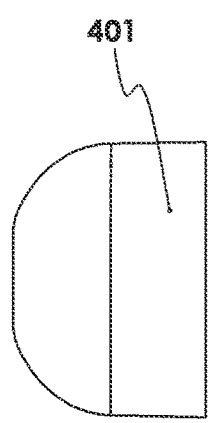
FIG. 4C depicts a side view of the dome cap of FIG. 4A, in accordance with an exemplary embodiment.

FIG. 4C illustrates an external side view of the dome cap. The dome cap can have a smooth or textured surface 401 and can be made of any number of thermoplastic or thermoset materials such as flexible PVC, thermoplastic elastomers, or silicone.

Figure 4D:
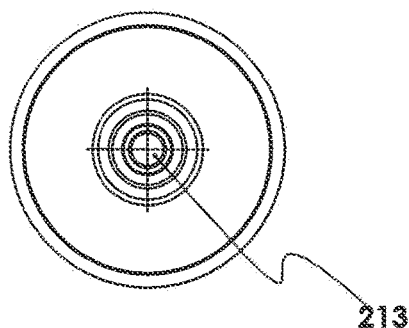
FIG. 4D depicts a bottom view of the dome cap of FIG. 4A, in accordance with an exemplary embodiment.

FIG. 4D illustrates the interior or bottom surface of the dome. The seal hub 213 is visible in the center of the dome. The seal hub makes an interference seal fit with the internal diameter of the valve stem to prevent air and/or water leakage.

Figure 4E:
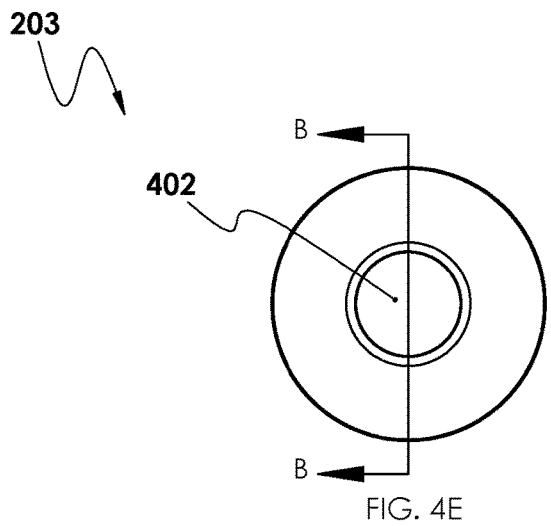
FIG. 4E depicts a top view of another possible embodiment of a dome cap for an air/water channel pre-cleaning adapter in accordance with an exemplary embodiment.
Figure 4F:
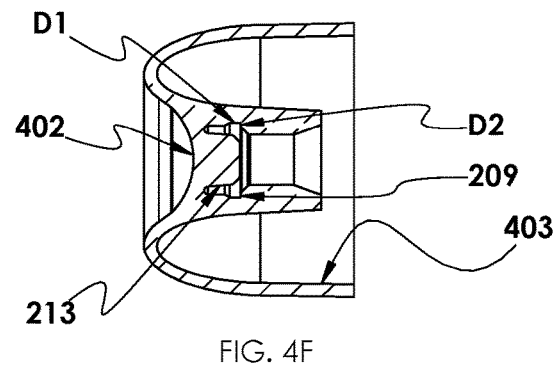
FIG. 4F depicts a cross section view of the dome cap of FIG. 4E, in accordance with an exemplary embodiment.

The recessed area can have one of a variety of shapes and sizes, described in detail herein. FIG. 4E illustrates another exemplary embodiment of a dome cap 203 having a large recessed area 402 located in the center of the top surface of the dome cap 203. In FIG. 4E, the recessed area is larger in size than the recessed area of FIG. 4A. FIG. 4F illustrates a cross-section view taken along line B-B in FIG. 4E. In FIG. 4F, the interior components such as the seal hub 213, interior wall surface 403, and lock feature 209 are shown.

Figure 4G:
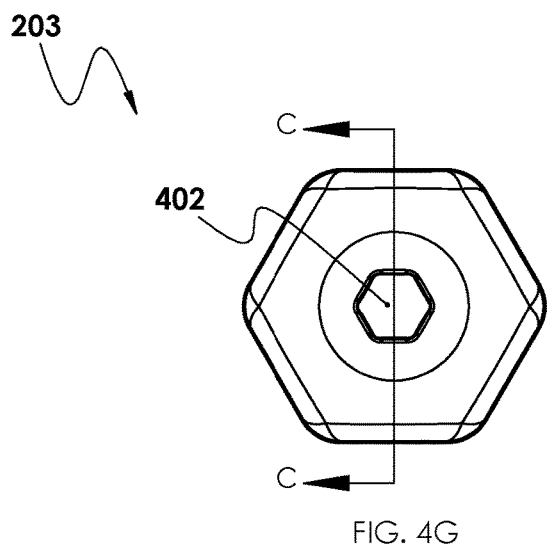
FIG. 4G depicts a top view of another possible embodiment of a dome cap for an air/water channel pre-cleaning adapter in accordance with an exemplary embodiment.
Figure 4H:
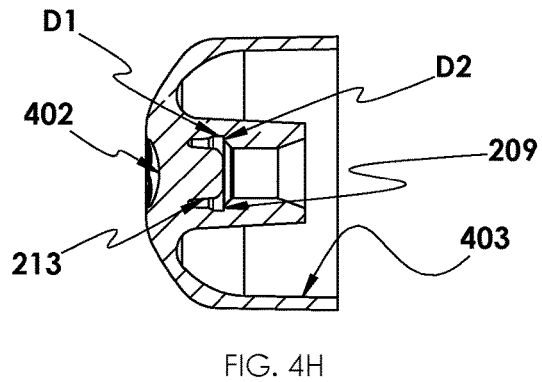
FIG. 4H depicts a cross section view of the dome cap of FIG. 4G, in accordance with an exemplary embodiment.

FIG. 4G illustrates another exemplary embodiment of a dome cap 203 having hexagonal sides and a hexagonal-shaped center recessed area 402. FIG. 4H illustrates a cross-section view taken along line C-C in FIG. 4G. In FIG. 4H, the interior components such as the seal hub 213, interior wall surface 403, and lock feature 209 are shown.

Figure 4J:
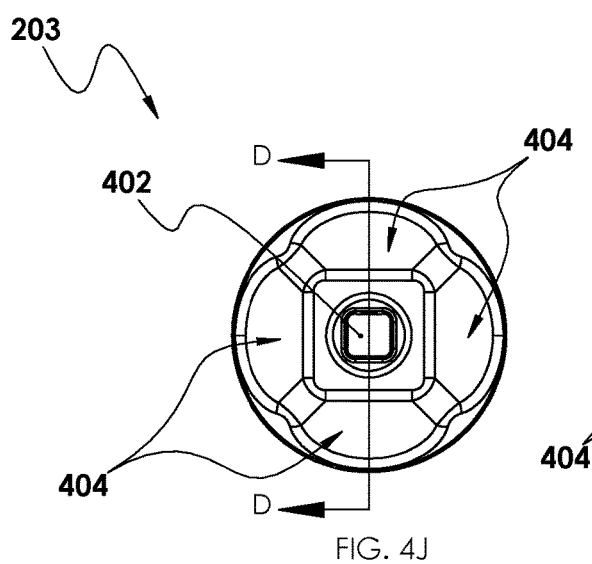
FIG. 4J depicts a top view of another possible embodiment of a dome cap for an air/water channel pre-cleaning adapter in accordance with an exemplary embodiment.
Figure 4K:
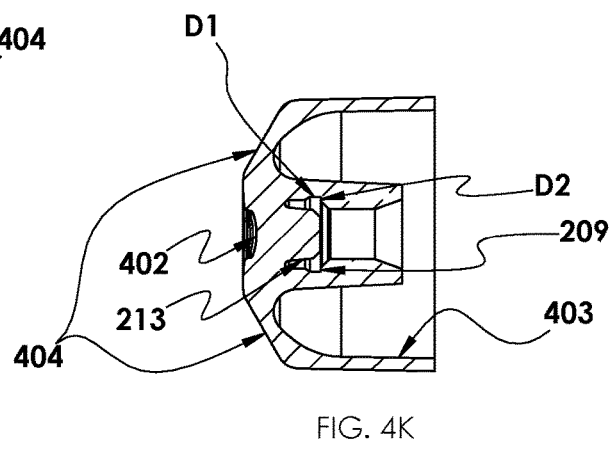
FIG. 4K depicts a cross section view of the dome cap of FIG. 4J, in accordance with an exemplary embodiment.

FIGS. 4J and 4K illustrate an exemplary embodiment of a dome cap 203 can have flattened portions 404 transitioning between the side wall and top, and a centrally-located recessed area 402 on the top surface can have a square shape. FIG. 4K illustrates a cross-section view taken along line D-D in FIG. 4J. In FIG. 4K, the interior components such as the seal hub 213, interior wall surface 403, and lock feature 209 are shown.

The interior surface 403 of each embodiment can have the same overall shape as the outer surface 401. Having the same overall shape however, is optional. The interior surface 403 can match the same overall shape as the outer surface of the base 201. The dome shape eliminates the need for coil spring(s). As explained above, when the dome is depressed to actuate the pre-cleaning adapter and then released, the dome will return to its original shape. As the dome returns to its original shape, the valve stem 202 that is secured to the dome by the lock feature is pulled back into a first position (at rest). When the button is in the at rest position, air will flow through the endoscope. When the dome button is actuated, water will flow.

Figure 5A:
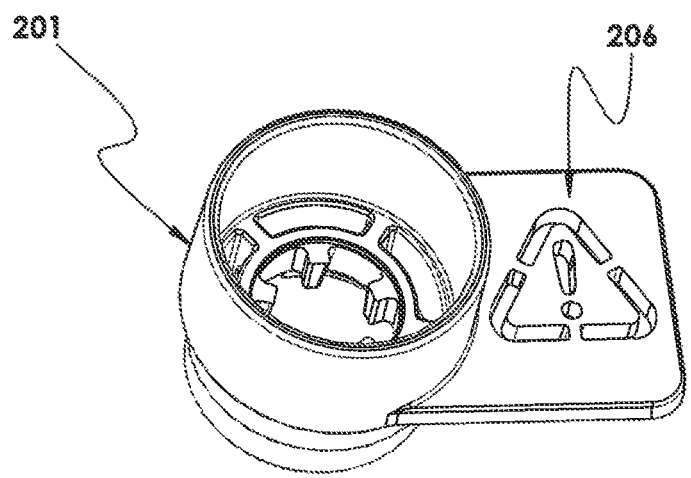
FIG. 5A depicts a valve base with an incorporated tag that has information in accordance with an exemplary embodiment.
Figure 5B:
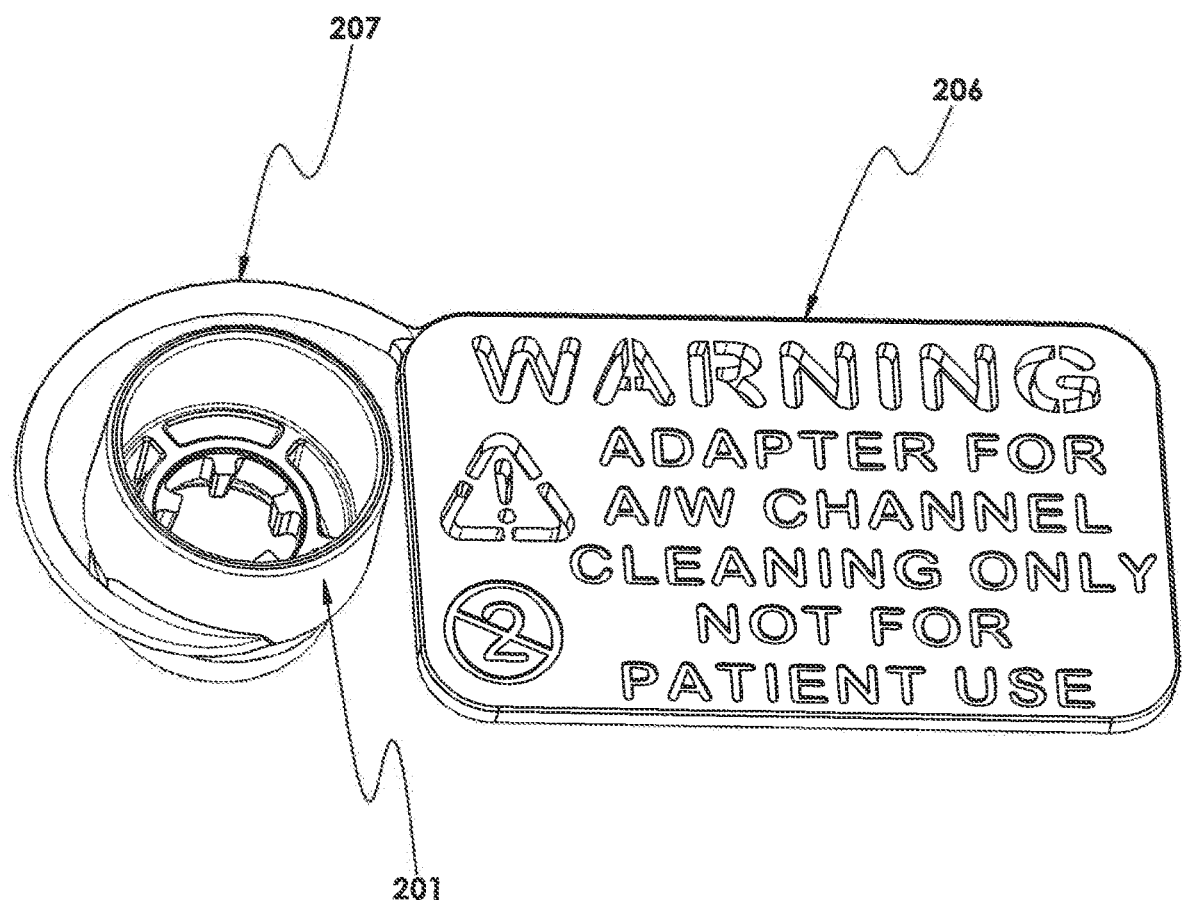
FIG. 5B depicts a valve base with a tag attached to it by a molded extender in accordance with an exemplary embodiment.
Figure 5C:
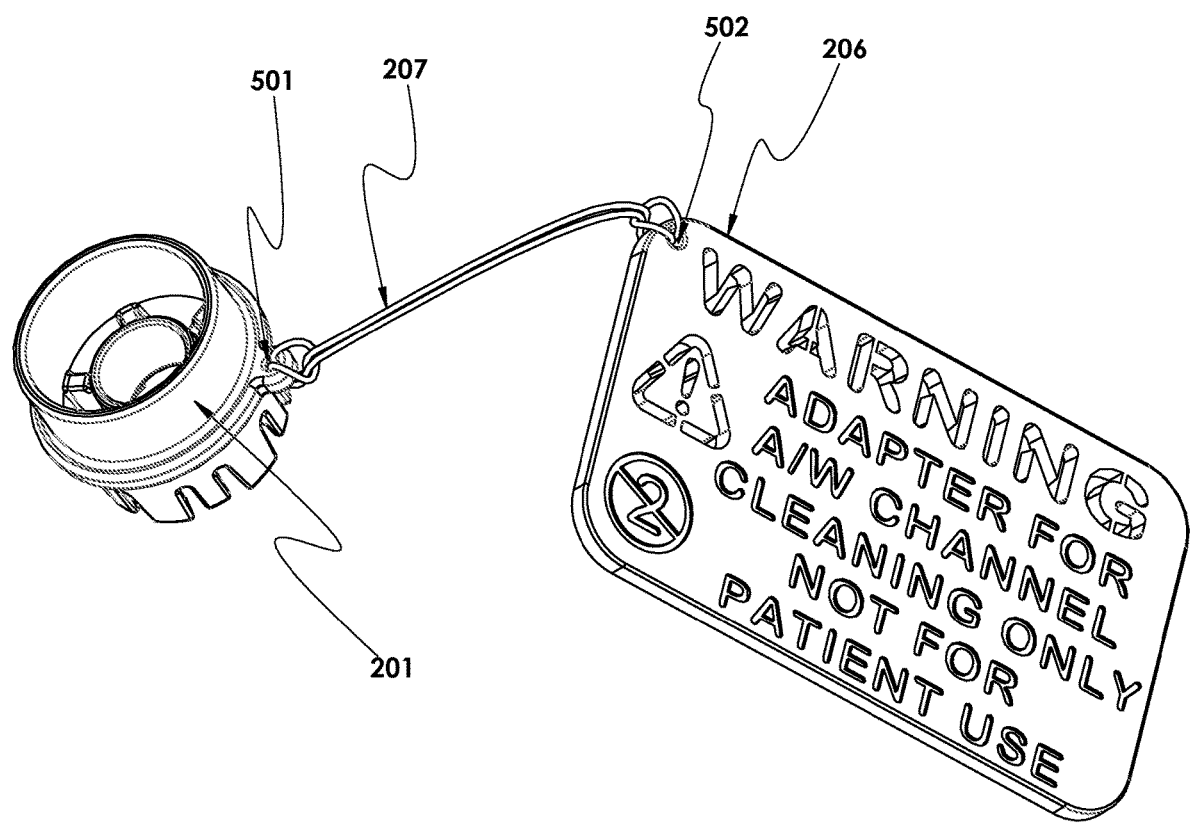
FIG. 5C depicts a valve base with a tag attached to it by a separate extender in accordance with an exemplary embodiment.
Figure 5D:
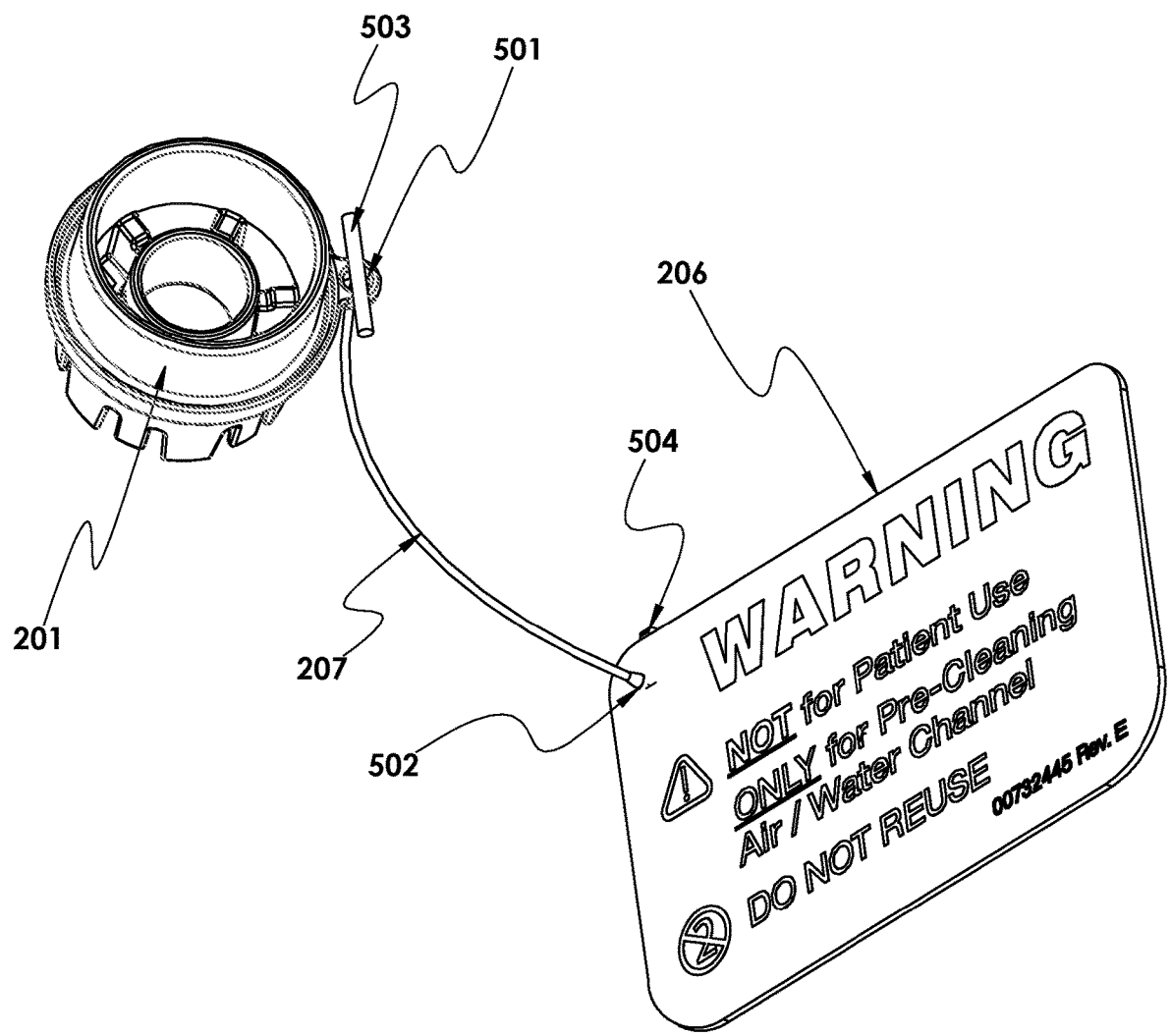
FIG. 5D depicts a valve base with a tag attached to it by another extender in accordance with an exemplary embodiment.

FIG. 5A illustrates a close-up view of a pre-cleaning adapter valve base 201 in accordance with an exemplary embodiment. The valve base can be cylindrical in shape with a proximal and distal end. FIG. 5A illustrates the base 201 from the distal surface view. In an exemplary embodiment, the tag 206 can be integrated into the base, as illustrated in FIG. 5A. FIG. 5B illustrates another embodiment where the tag is connected to the base by a molded extender. In FIG. 5B, the extender 207 can be of the same material as the tag 206 and/or base 201. The extender, base, and tag can be integrated, and can be made from one mold. The extender 207 can separate the tag from the base by the length of the extender. FIG. 5C illustrates another embodiment where the tag is attached to the base by an extender 207 that is a separate piece of material. The separate extender 207 can be a tether or an elongate element, such as a thread or string, and can be made of a polymer or other material. The separate extender can be attached to the base 201 by threading it through a hole 501 in the base 201 and by threading it through a hole 502 in the tag 206. The separate extender 207 can be tied or twisted to secure it. FIG. 5D illustrates another embodiment where the tag is attached to the base by a separate extender 207 that is an elongated member such as a retail price tag attachment. The retail price tag attachment can have a first anchor 503 and a second anchor 504. The first anchor can be inserted through hole 501 on the base 201. The second anchor 504 can be inserted through the hole 502 on the tag 206. The tag can have any one or more of a plurality of information, messages, or warnings provided on it. In the embodiment illustrated in FIG. 5A, the tag can display a universal warning symbol.

Figure 5E:
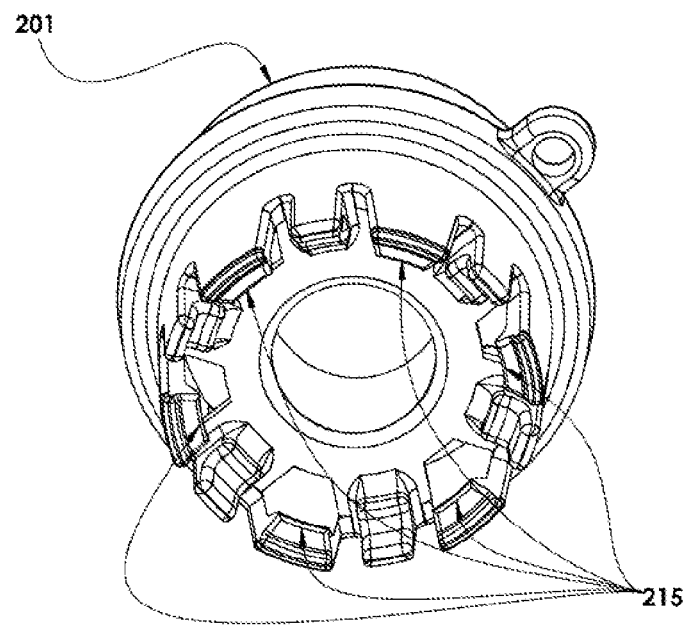
FIG. 5E depicts locking tabs extending from a distal end of the valve base in accordance with an exemplary embodiment.
Figure 5F:
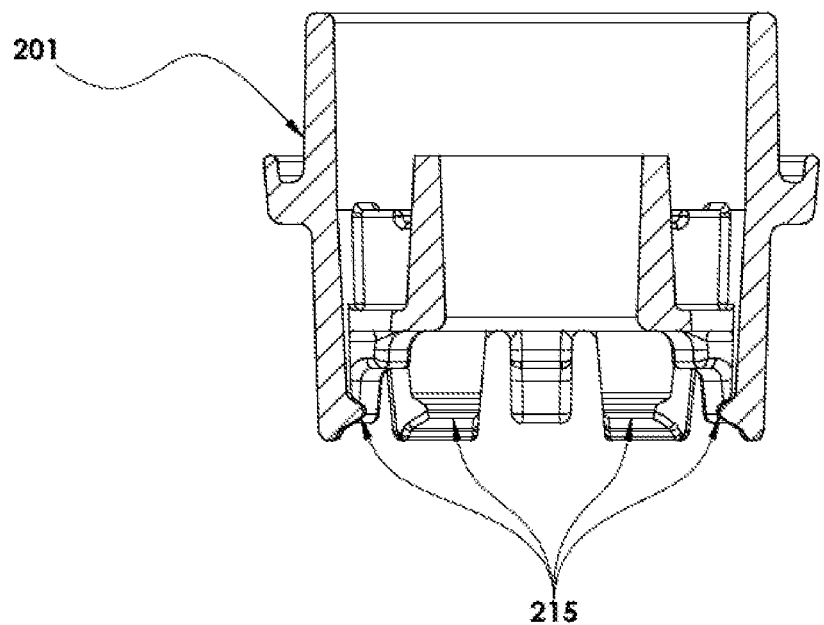
FIG. 5F depicts a sectional view of a valve base having locking tabs in accordance with an exemplary embodiment.
Figure 5G:
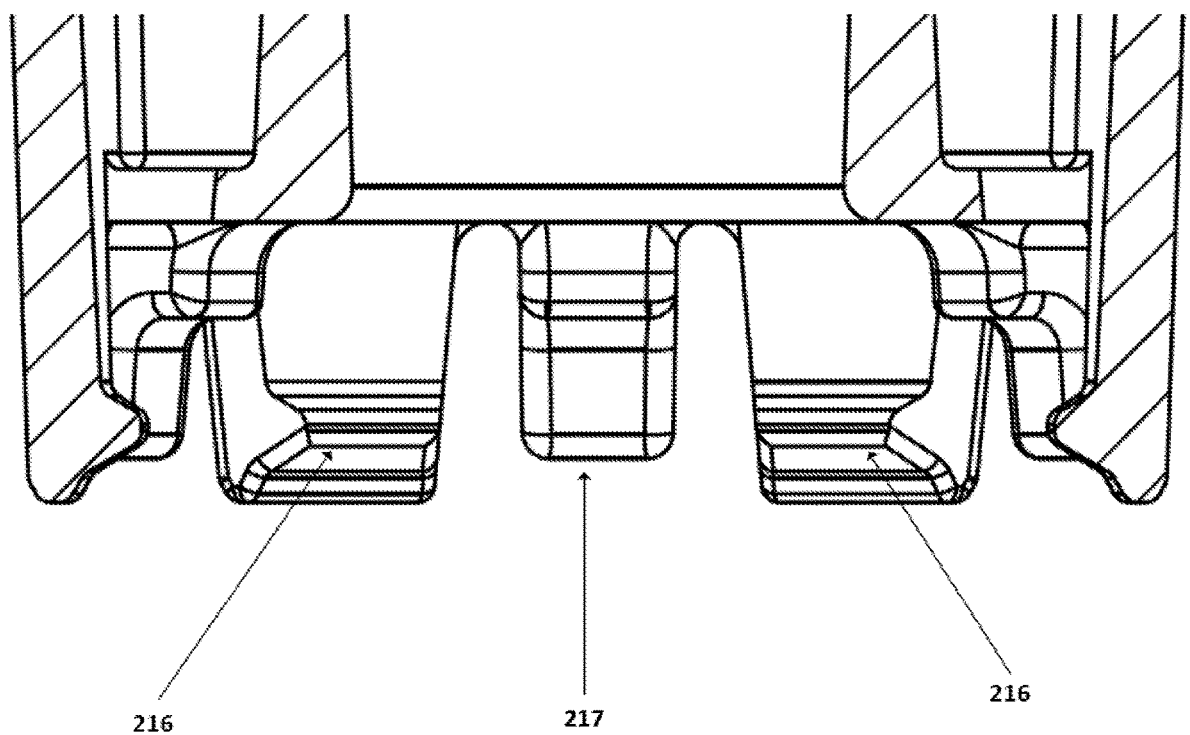
FIG. 5G depicts a close-up view of a valve base having locking tabs in accordance with an exemplary embodiment.

Referring to FIGS. 5E and 5F, the valve base 201 can include a plurality of locking tabs 215 extending downwardly from a distal end of the valve base 201. The locking tabs 215 are configured to be inserted into a plurality of apertures (not shown) formed in a proximal end of a separate air/water cylinder. In this respect, the locking tabs 215 are configured to secure the pre-cleaning adapter valve 200 to the air/water cylinder. In one exemplary embodiment, the locking tabs 215 can embody resilient fingers having inwardly facing protrusions 216 (FIG. 5G) that can be snapped into place (e.g., into recesses formed in side walls of a receiving element of the air/water cylinder). The locking tabs 215 can also include vertically protruding guide elements 217 that help align the valve base 215 onto the air/water cylinder. However, it is contemplated that other configurations of locking tabs 215 can be employed (e.g., clasps, snaps, fasteners, etc.). The locking tabs can be a part of any valve base embodiment described herein.

Figure 2D:
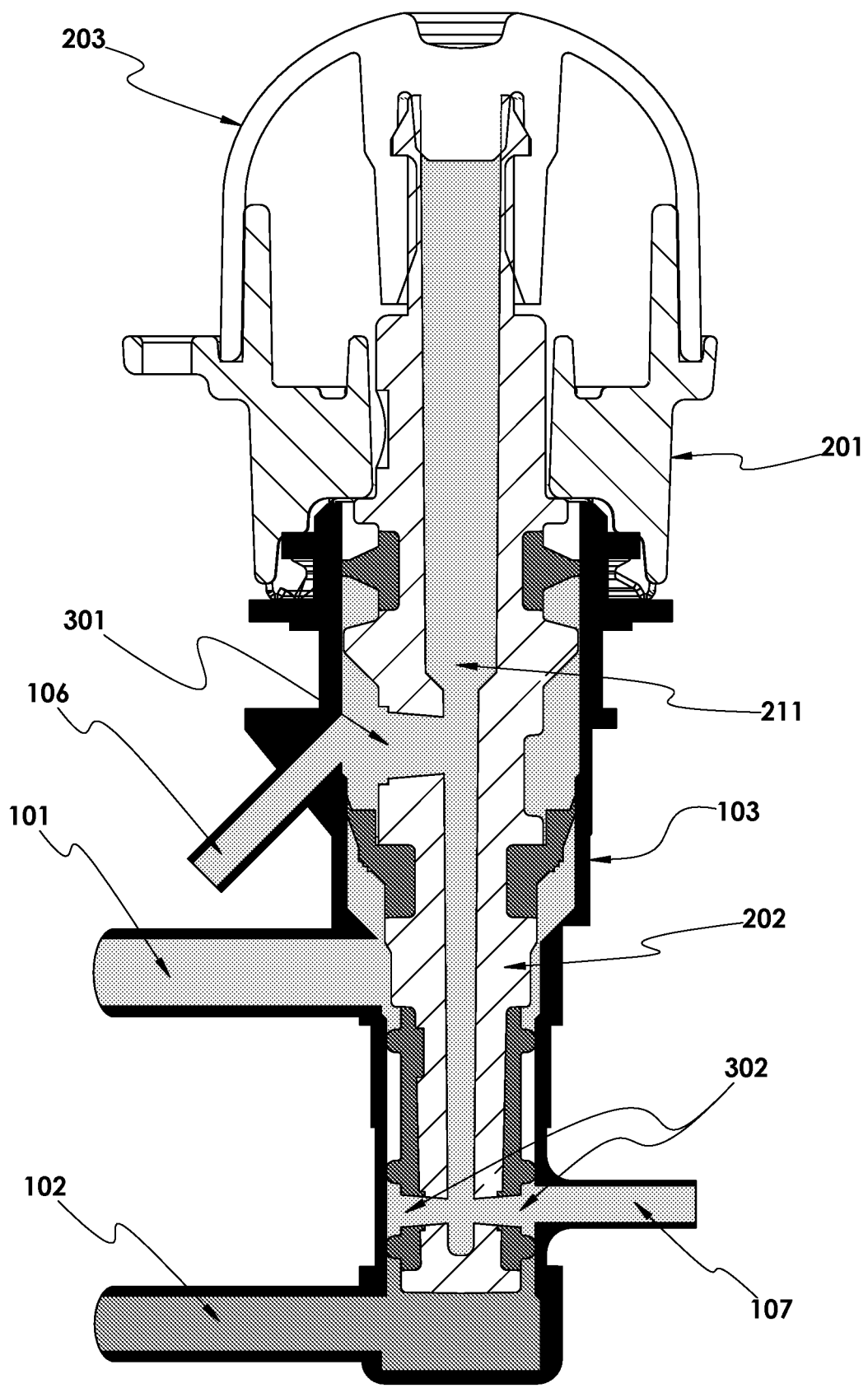
FIG. 2D depicts a schematic of an air/water channel pre-cleaning adapter in a first position (at rest) in accordance with an exemplary embodiment.
Figure 2E:
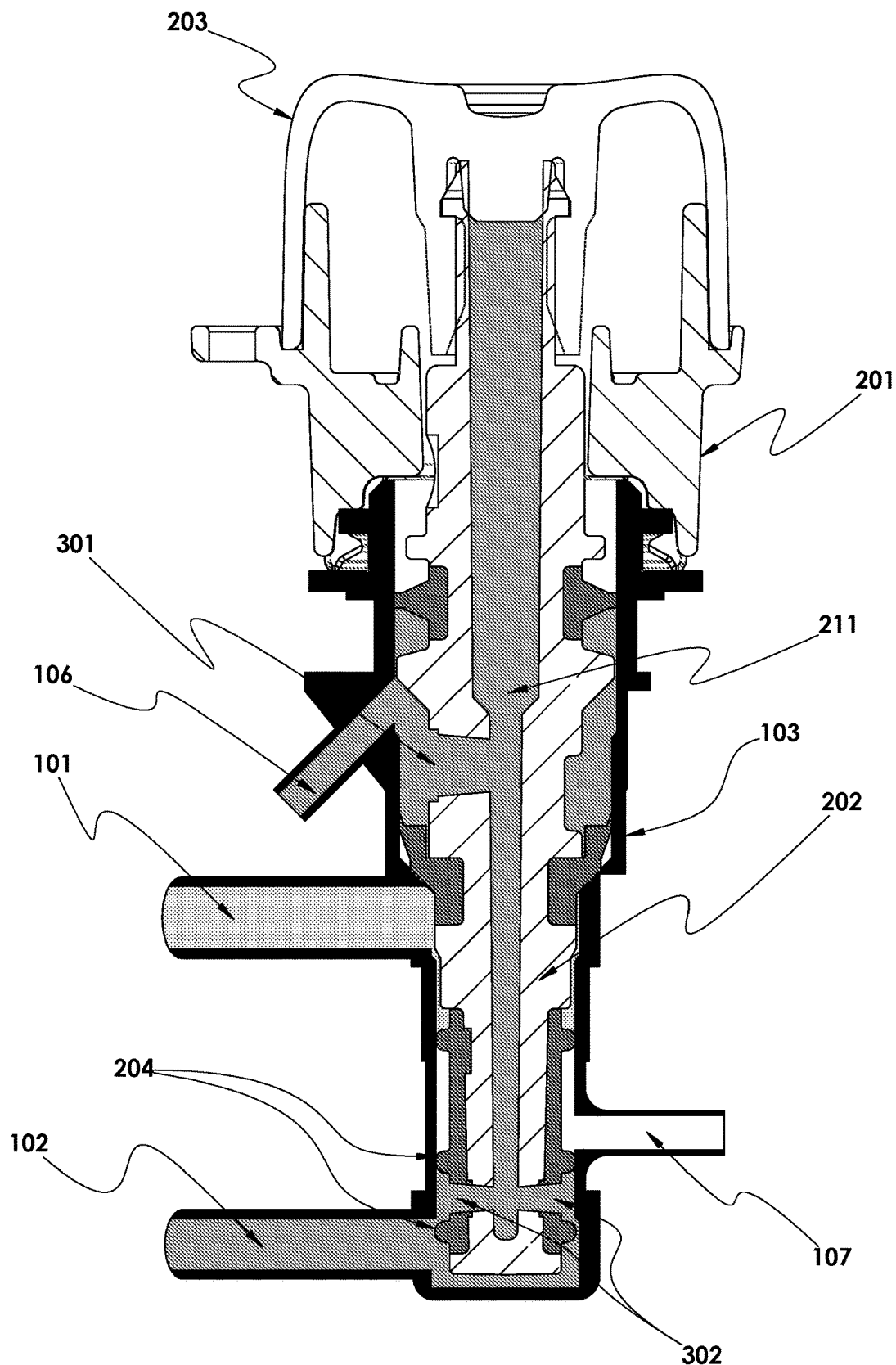
FIG. 2E depicts a schematic of an air/water channel pre-cleaning adapter in an actuated position in accordance with an exemplary embodiment.

FIGS. 2D and 2E illustrate schematics of an exemplary embodiment having first and second positions. In the first position, FIG. 2D, where the button 203 is at rest, and air is free to flow through proximal side hole 301 into the central stem channel 211 and out through distal side holes 302. In this at rest position, the valve stem 202 allows air to flow from air channel 101 through the proximal exit port 106 and distal exit port 107 to the distal end of the endoscope. Water from water channel 102 does not flow. In the second position, FIG. 2E, where the button 203 is actuated, the valve stem is pushed in a distal direction, permitting water to flow from water inlet 102 through the distal side holes 302 into the central valve stem channel 211 and out through the proximal side hole 301. In this position, water is permitted to flow through the proximal exit port 106 to the distal end of the endoscope. In this position, air from inlet 101 does not flow.

Figure 6:
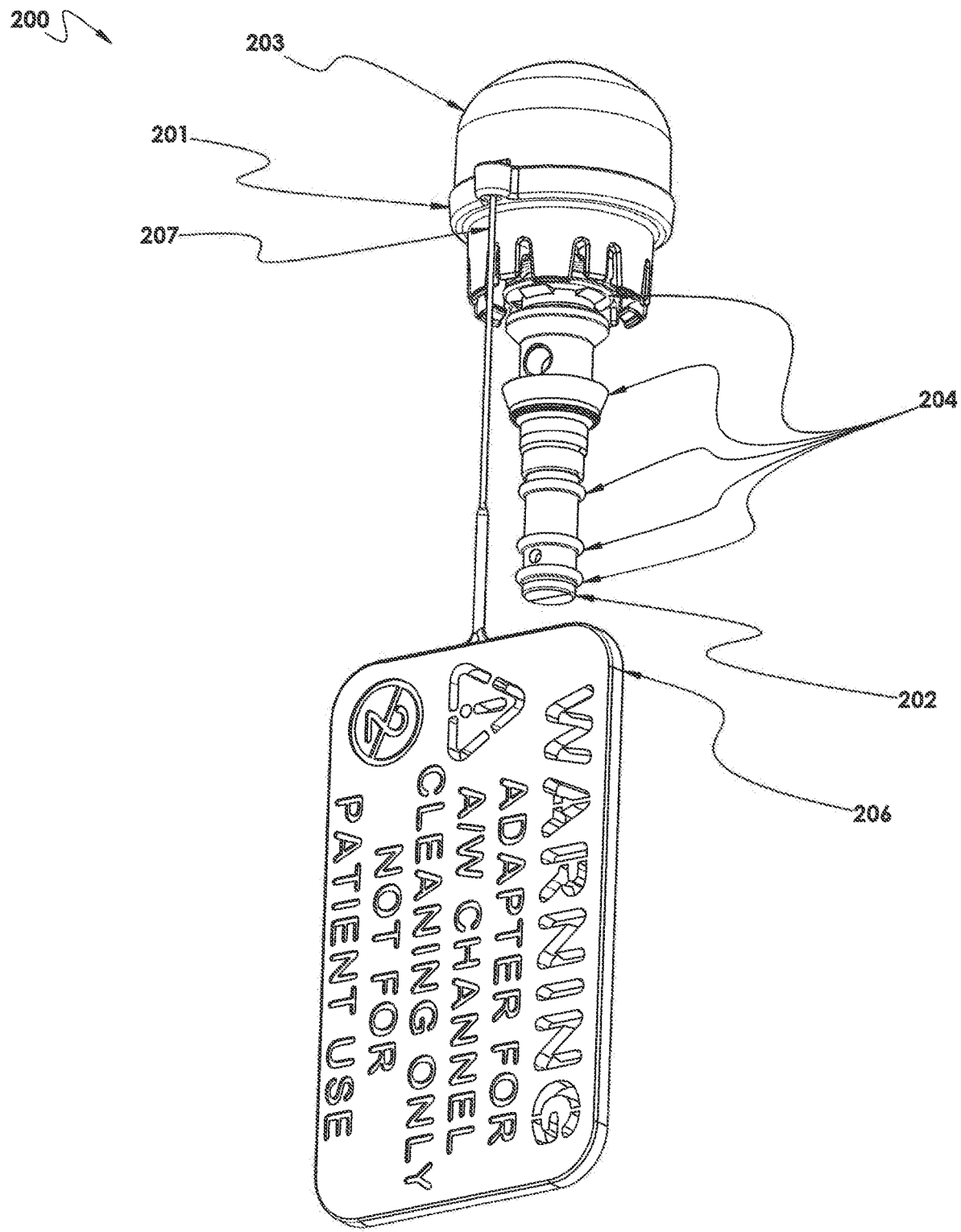
FIG. 6 depicts an air/water channel pre-cleaning adapter having a tag in accordance with an exemplary embodiment.

FIG. 6 illustrates an exemplary embodiment of an air/water pre-cleaning adapter valve 200 having a dome cap 203 and a tag 206 that is connected to the base 201 by an extender 207. In FIG. 6, the attachment line can be injection molded. It can be snap-fit into the base 201 or threaded to screw-fit into the base. Additional embodiments for the tag include injection molding it as one with the base; thermoformed and snapped into place; die cut from a sheet stock and/or snapped, glued, or threaded into place, or any other embodiment as described above.

Figure 7A:
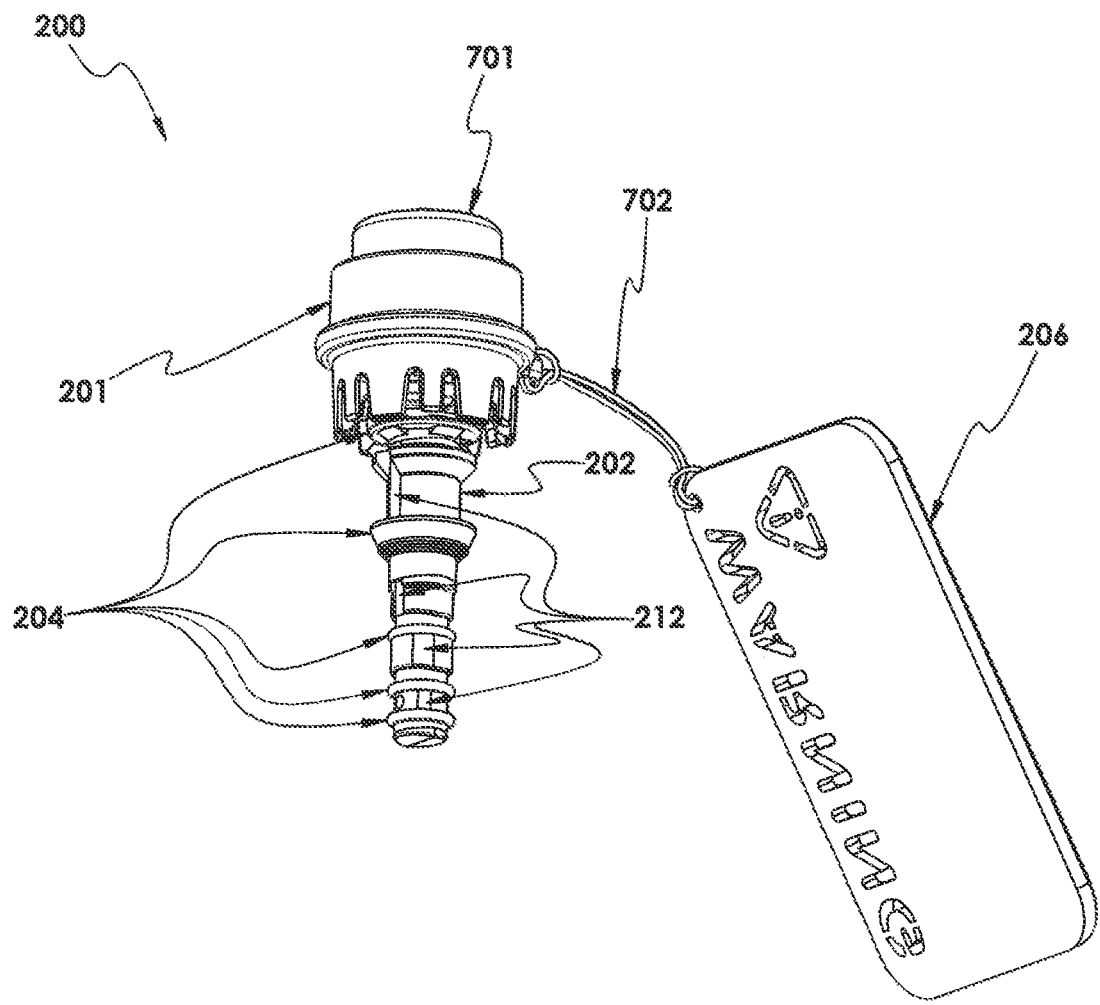
FIG. 7A depicts an air/water channel pre-cleaning adapter having a button cap in accordance with an exemplary embodiment.
Figure 7B:
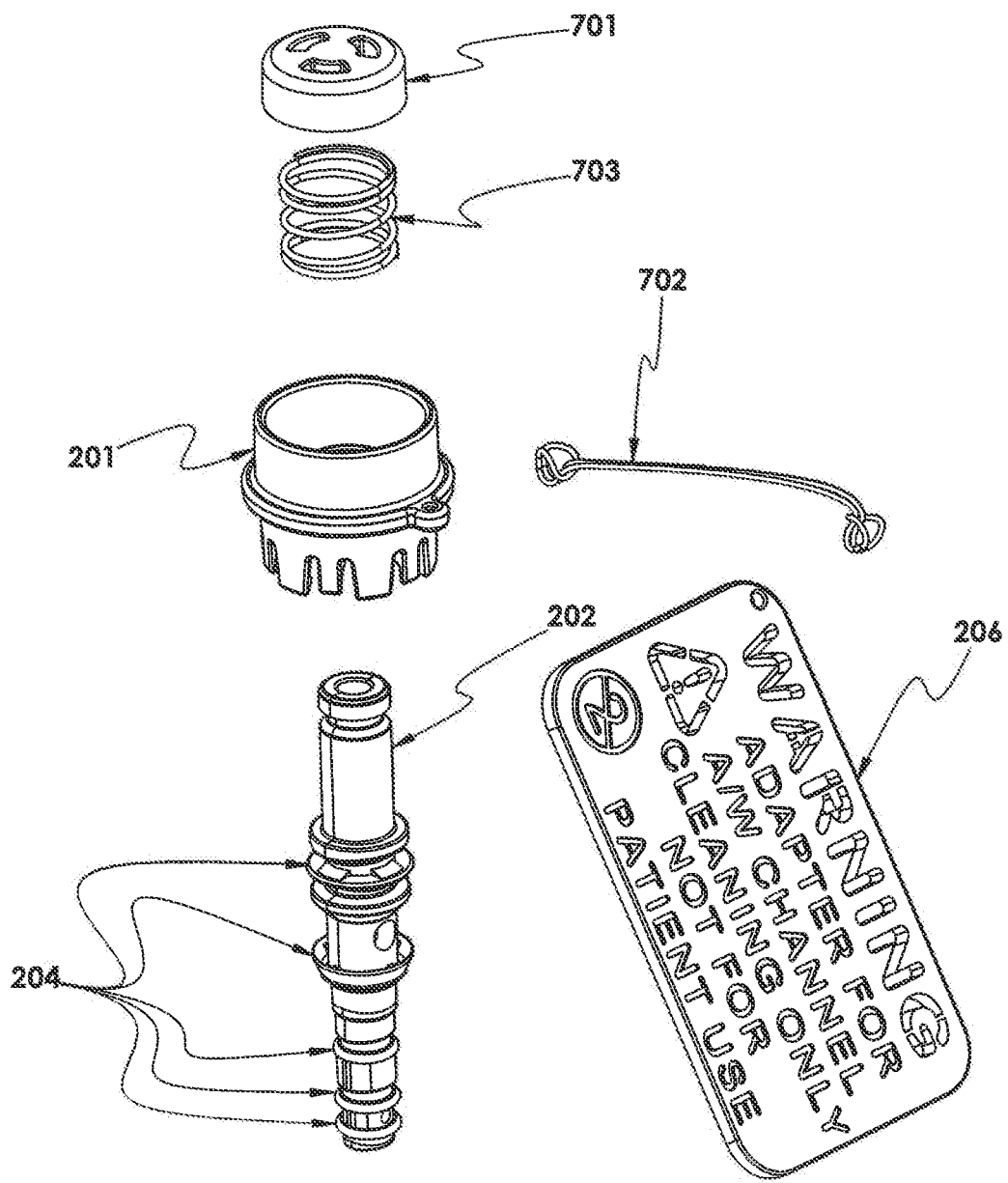
FIG. 7B depicts an exploded view of the air/water channel pre-cleaning adapter of FIG. 7A, in accordance with an exemplary embodiment.
Figure 7C:
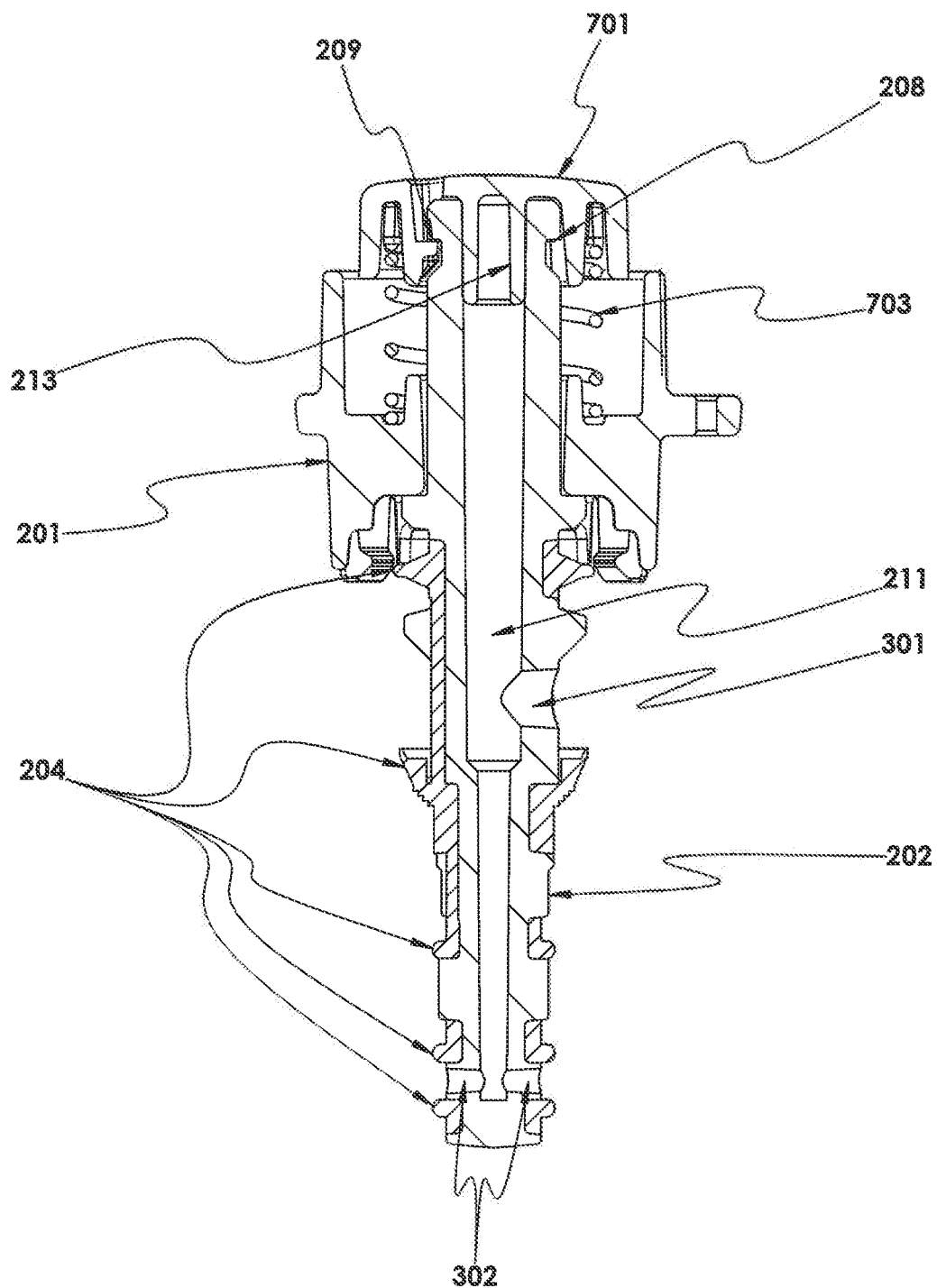
FIG. 7C depicts a cross-section view of an air/water channel pre-cleaning adapter of FIG. 7A, in accordance with an exemplary embodiment.

FIGS. 7A-C illustrate an exemplary embodiment of an air/water pre-cleaning adapter valve 200 having a button cap 701. Similar to the other embodiments described herein, the button cap embodiment of the pre-cleaning adapter valve 200 can have gaskets 204 to provide a seal, a valve base 201, and a tag 206. In FIG. 7A, the distal seals 204 can be molded from the same piece of material, in which the individual gaskets are connected by a connecting strip 212. In FIG. 7A, the tag is connected to the valve base with a loop or string cable 704. The tag 206 can be connected to the valve base 201 by any of the means described herein.

FIG. 7B illustrates an exploded view of the components of the device in FIG. 7A. The button 701 can be molded from any number of thermoplastic or thermoset materials such as ABS, polyethylene, polypropylene, polycarbonate, or diallyl phthalate. The button is positioned over the end of a coiled spring 703, which can be made of stainless steel. The coiled spring 703 fits into an inner cylindrical shape of the valve base, which can be molded. The valve stem 202, which can also be molded, extends out the other/proximal end of the valve base. FIG. 7C illustrates a cross-section view of the air/water pre-cleaning adapter valve device embodiment of FIG. 7A. FIG. 7C illustrates the valve stem, and that it extends from a proximal end where it is connected to the button cap 701 to a distal end that fits into a channel on an endoscope. The valve stem 202 has an elongate channel 211 running therethrough, for air and/or water to pass through. The elongate channel also has two openings 301, 302 on the side, that extend through the valve stem 202 to permit flow of air and/or water. The configuration of the elements can be similar as that in the dome cap embodiment, as illustrated in FIGS. 2A-2C and described above.

Figure 8A:
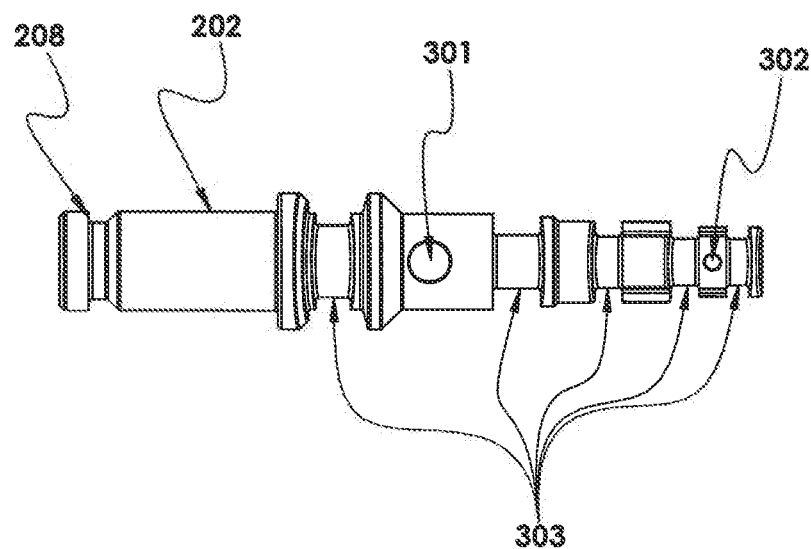
FIG. 8A depicts another possible valve stem of an air/water channel pre-cleaning adapter in accordance with an exemplary embodiment.
Figure 8B:
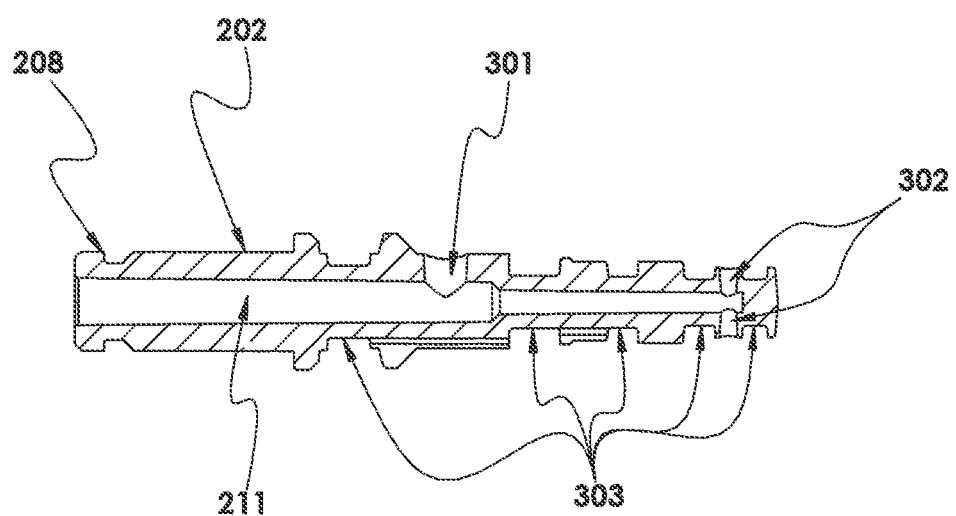
FIG. 8B depicts a cross section view of the valve stem of FIG. 8A, in accordance with an exemplary embodiment.

FIGS. 8A-B illustrate in further detail the valve stem for an exemplary embodiment of an air/water pre-cleaning adapter valve. The valve stem 202 can have indentations or grooves 303 positioned cylindrically around the outer surface of the stem. These grooves are for placement of the gaskets 204. The proximal portion of the valve stem 202 can have a proximal groove that can interlock with a locking feature 209 of the button cap 701. The configuration of the elements can be similar as that in the dome cap embodiment, as illustrated in FIGS. 3A and 3B and described above.

FIGS. 9A-D illustrate in greater detail a button cap for an air/water pre-cleaning adapter valve in accordance with an exemplary embodiment. FIG. 9A illustrates a proximal outer surface of a button endcap in accordance with an exemplary embodiment, which is the interface that can be pressed by a user to actuate the pre-cleaning adapter valve. Holes 901 can be present in an exemplary embodiment of the button cap to mold snap features to lock the button to the valve stem. In an exemplary embodiment, there can be three holes 901 to provide three mold snap features 902. The number of holes and corresponding snap lock features can range from two (2) to eight (8). In other exemplary embodiments, other attachment features can be present instead of holes and mold snap features.

In the cross-sectional view as illustrated in FIG. 9B, the seal hub 213 extends in a distal direction out from the button cap. The seal hub can consist of a hollow interior portion or it can be solid. The lock feature 209 can be a protrusion extending inwardly around an inner circumference of the button cap, interlocking with locking feature 208 on the valve stem.

There can be a spring retainer, which can be formed by an indentation extending from the distal end towards the proximal end, in the button cap, that can encircle the entire circumference of the cap. The spring retainer can be an outer ring 903 defining an outer edge of the indentation and an inner ring 904 defining the inner edge of the indentation. A proximal end of a coiled spring can be fit into the indentation and retained between the two rings. FIG. 9D illustrates the location of the two rings 903, 904. The seal hub 213 can be centrally located on the distal end of the button cap 701, as illustrated in FIG. 9D, and can have a central opening 905 making it substantially hollow inside. The interference seal that can be made between the seal hub 213 and the inner diameter of the valve stem 202 can prevent air and/or water leakage.

FIG. 9C illustrates the outer surface of the button cap 203. The outer surface can be smooth.

The air/water pre-cleaning adapter with a button cap can also have an automatic shut-off feature. Similar to the time delay feature on automatic faucets, the automatic shut-off feature can be set to switch the valve stem in the adapter from a distal position (as shown in FIG. 2E) in which water flows through the adapter to a proximal position (as shown in FIG. 2D) in which air flows through the adapter, after a predetermined amount of time has passed. In another embodiment, the valve stem can be moved from the distal position to the proximal position after a predetermined volume of fluid flow has passed through the valve. The system of claim 21, wherein pressing the button in a distal direction moves the valve stem from the proximal position to the distal position relative to the base, wherein the system further comprises an automatic shut-off feature wherein the valve automatically returns from the distal position to the proximal position after a predetermined amount of time. The automatic shut-off feature can be applied to any of the embodiments described herein, including but not limited to the embodiment having a toggle switch, as described in FIGS. 10A-10F.

As with any embodiment described herein, the button cap air/water pre-cleaning adapter valve can have a tag 206 attached to it by any of the means described herein.

Figure 10A:
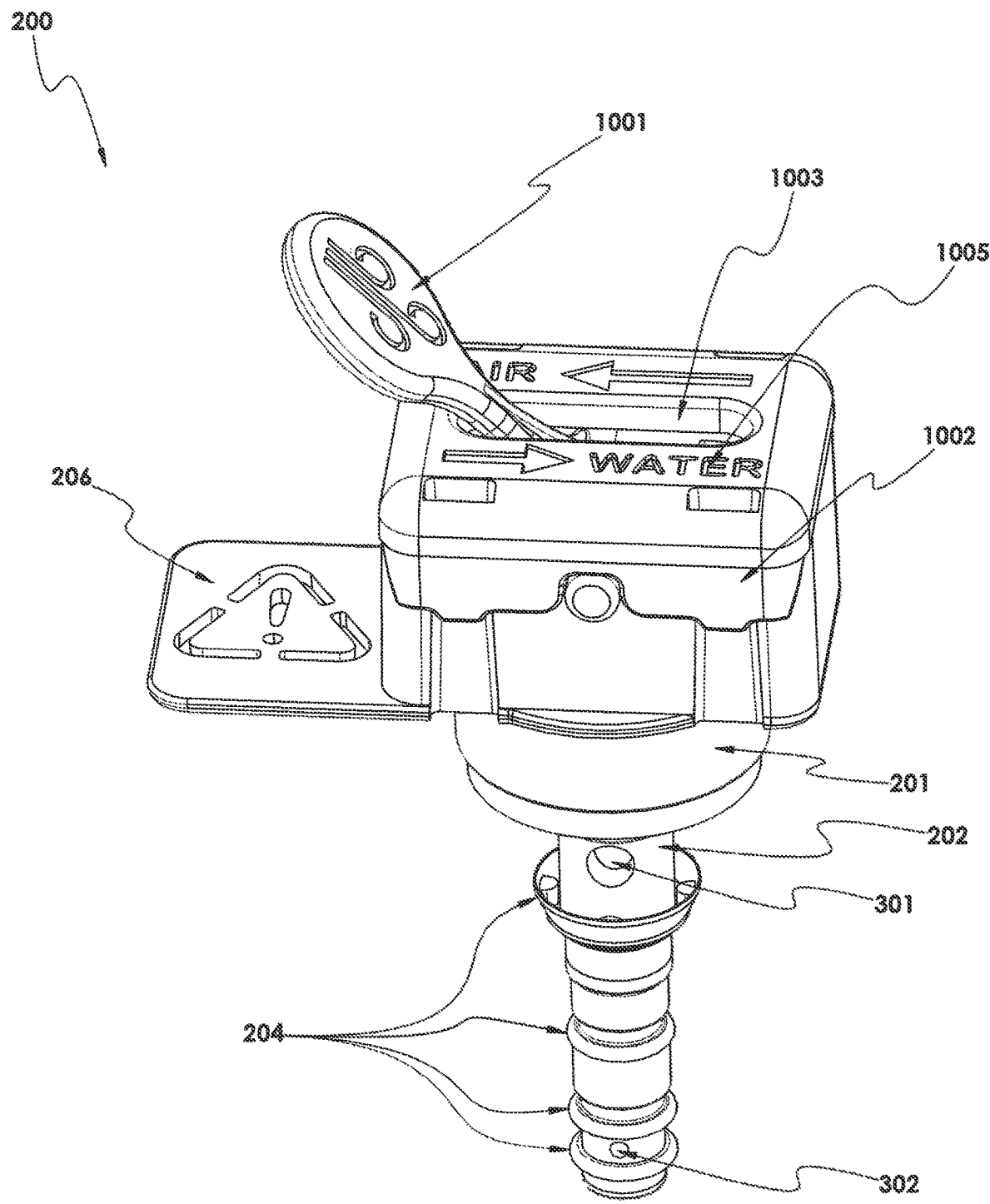
FIG. 10A depicts an air/water channel pre-cleaning adapter having a toggle switch in accordance with an exemplary embodiment.

FIGS. 10A-F illustrate an exemplary embodiment of an air/water pre-cleaning adapter valve 200 having a toggle switch 1001 and cam 1007. The toggle switch can eliminate user fatigue that typically occurs when a user holds the pre-cleaning adapter in a depressed state during pre-cleaning of an endoscope. The components of this embodiment include a valve cap 1002 that can have a substantially flat surface with an opening 1003 through which the arm of the toggle 1001 extends through. The top surface 1005 of the valve cap can have markings indicating "air" and "water" so a user can easily determine which way to move the toggle based on the desired function at any given time. The toggle switch 1001 is a lever arm connected to the valve mechanism. The toggle embodiment can utilize a functionally similar internal portion to other embodiments described herein and have a valve stem with gaskets and a valve body with a tag attached. FIG. 10A illustrates an exemplary embodiment of the toggle switch air/water pre-cleaning adapter valve 200 with the toggle switch 1001 set to the "air." With the toggle switch, the two positions it can be set to are "air" and/or "water."

Figure 10B:
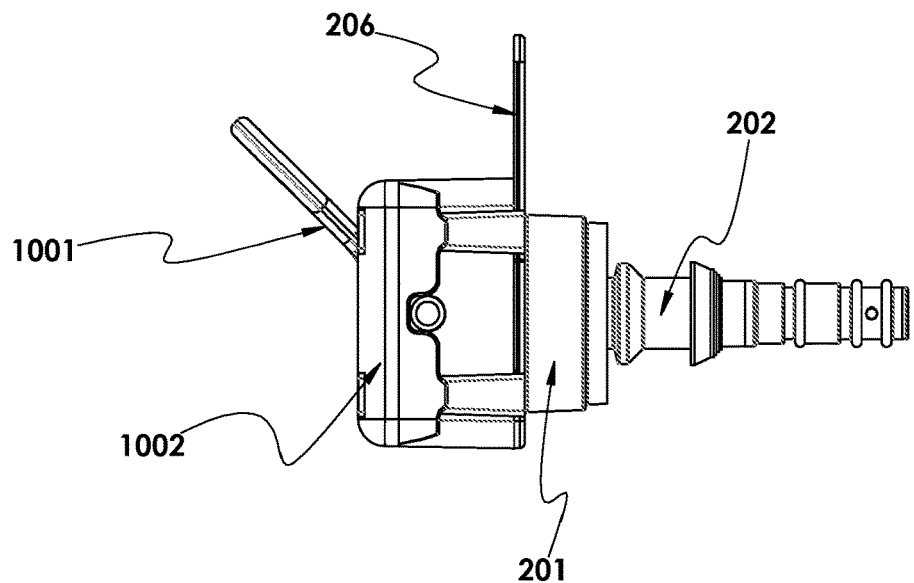
FIG. 10B depicts a side view of the air/water channel pre-cleaning adapter of FIG. 10A.
Figure 10C:
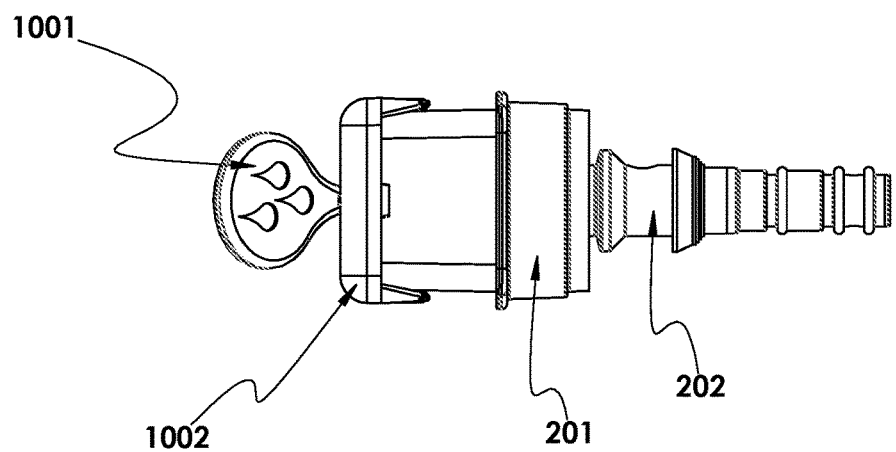
FIG. 10C depicts a front view of the air/water channel pre-cleaning adapter of FIG. 10A.

The toggle switch can be set to allow air to flow through when it is pulled to a first side. The toggle switch can be set to allow water to flow through when it is pulled to a second side. FIG. 10B illustrates a side view of the toggle switch air/water pre-cleaning adapter valve. In this embodiment, the "air" setting is on the same side as the tag 206, but any embodiment of tag and location is acceptable, and this is merely exemplary. FIG. 10C illustrates a rear view of the toggle embodiment, also in the "air" position.

Figure 1C:
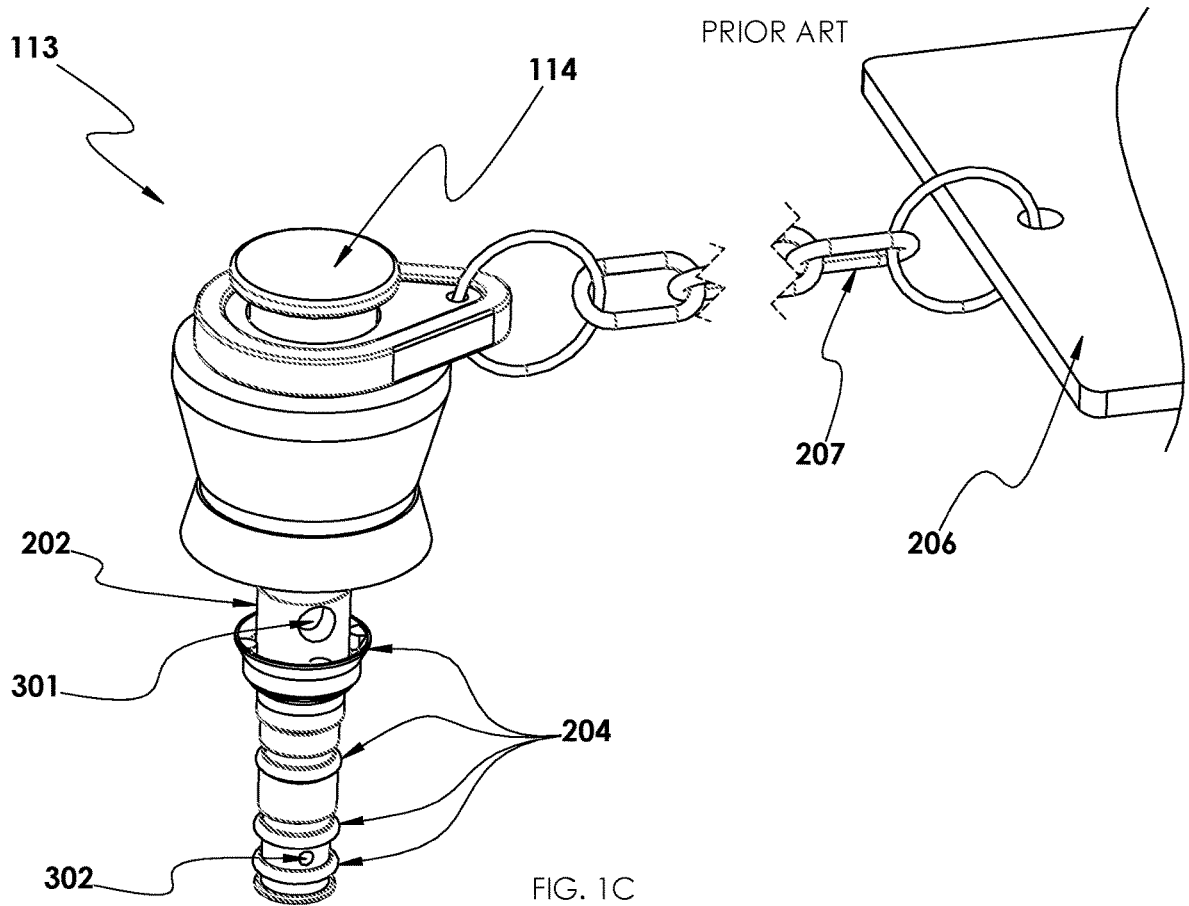
FIG. 1C depicts a prior art air/water channel cleaning adapter valve.
Figure 10D:
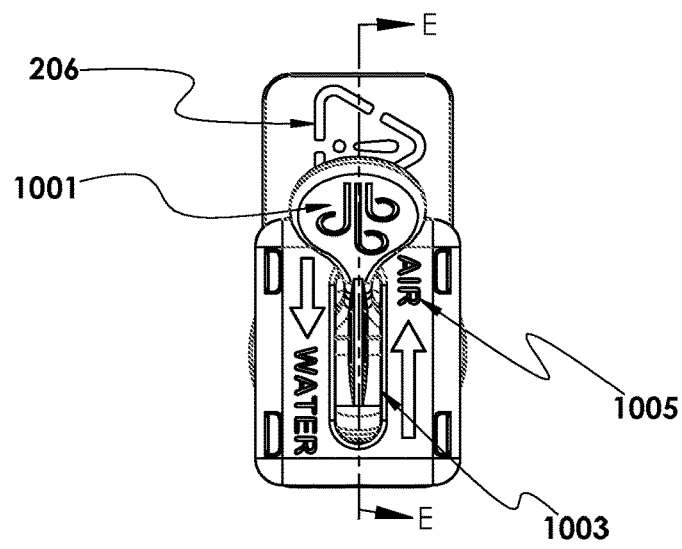
FIG. 10D depicts a top view of the air/water channel pre-cleaning adapter of FIG. 10A.
Figure 10E:
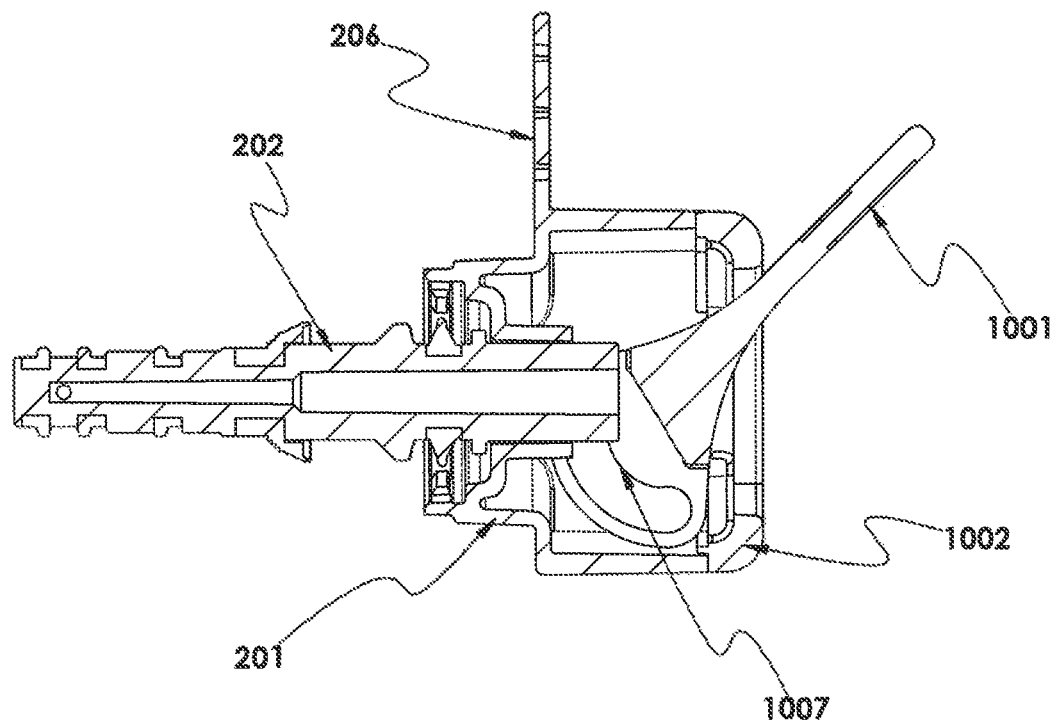
FIG. 10E depicts a cross-section view of the air/water channel pre-cleaning adapter of FIG. 10A in a first position (at rest) in accordance with an exemplary embodiment.
Figure 10F:
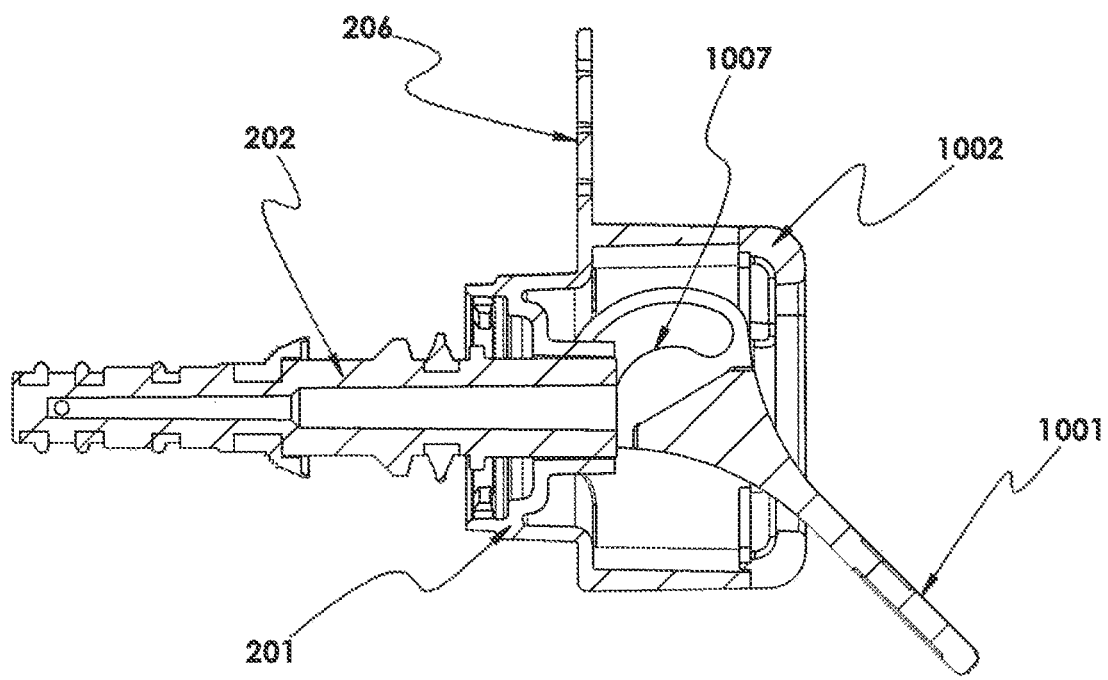
FIG. 10F depicts a cross-section view of the air/water channel pre-cleaning adapter of FIG. 10A in a second (actuated) position in accordance with an exemplary embodiment. [0053]

FIG. 10D illustrates a top view of the toggle assembly embodiment in the "air" flow position. Line E-E illustrates where the cross-section view illustrated in FIGS. 10E and 10F are taken from. The toggle switch can have a cam on its distal end that is slidably connected to the proximal end of the valve stem 202. FIG. 10E illustrates the toggle switch 1001 in the "air" position. In this position, the valve channel is internally open so that air can flow through the endoscope. The cam 1007 is in a first position that holds the valve stem up, or proximal, with respect to the base 201. This position functions the same as described for FIG. 2D above. FIG. 10F illustrates the same pre-cleaning adapter in the "water" position where the cam 1007 has shifted and the valve stem has moved in a distal direction with respect to the base 201. This position provides the same function as described for FIG. 2E above. Thus, the toggle switch only requires the user to contact the switch when the flow is to change from air to water, or from water to air. Contact with the switch is not required for pre-cleaning operation of the air/water pre-cleaning adapter valve, unlike the prior art of FIG. 1C which requires a user to hold down on the button.

Figures 11A, 11B:
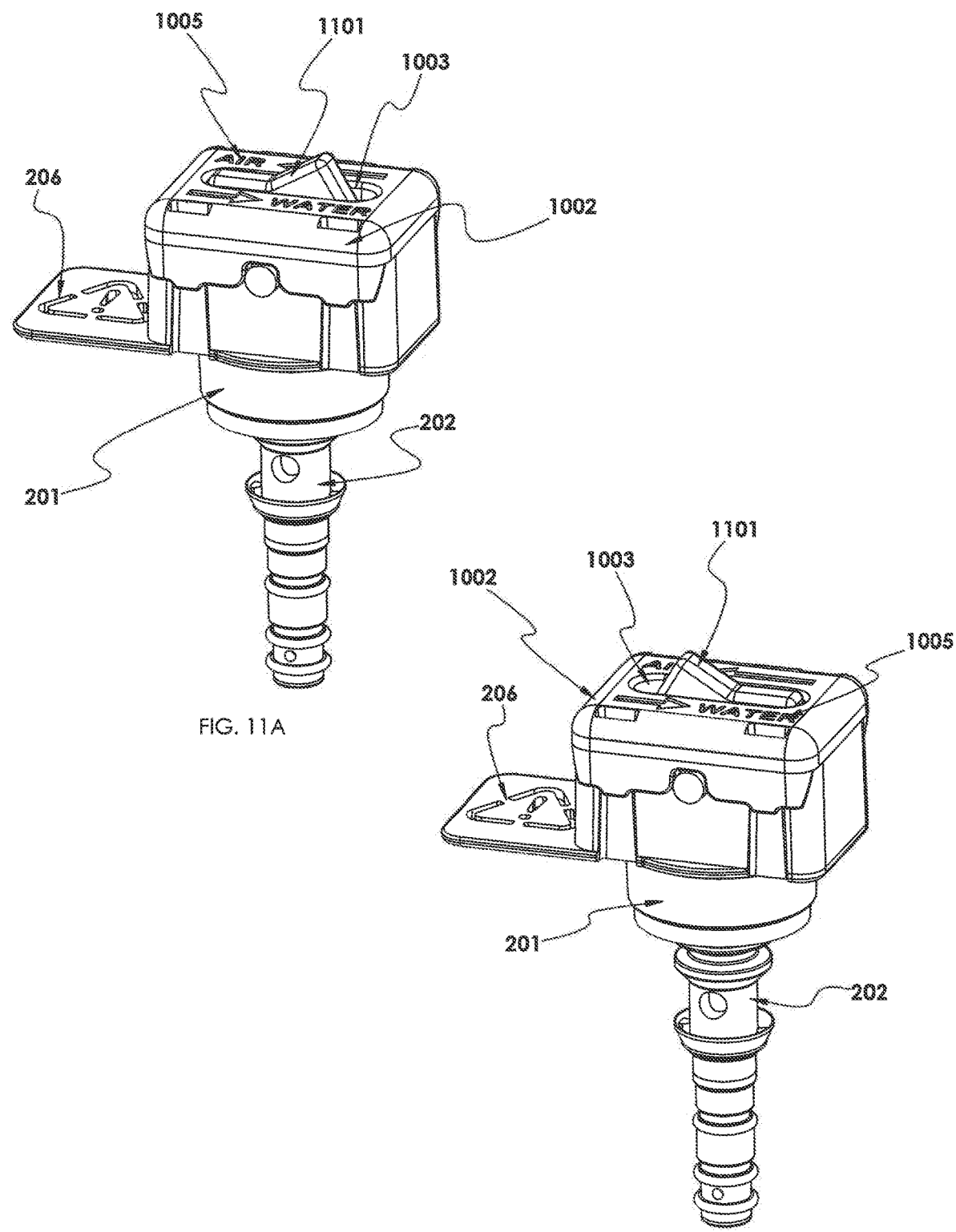
FIG. 11A depicts a switch for an air/water channel pre-cleaning adapter in a first position (at rest) in accordance with an exemplary embodiment.
FIG. 11B depicts a switch for an air/water channel pre-cleaning adapter in a second (actuated) position in accordance with an exemplary embodiment.
Figure 11C:
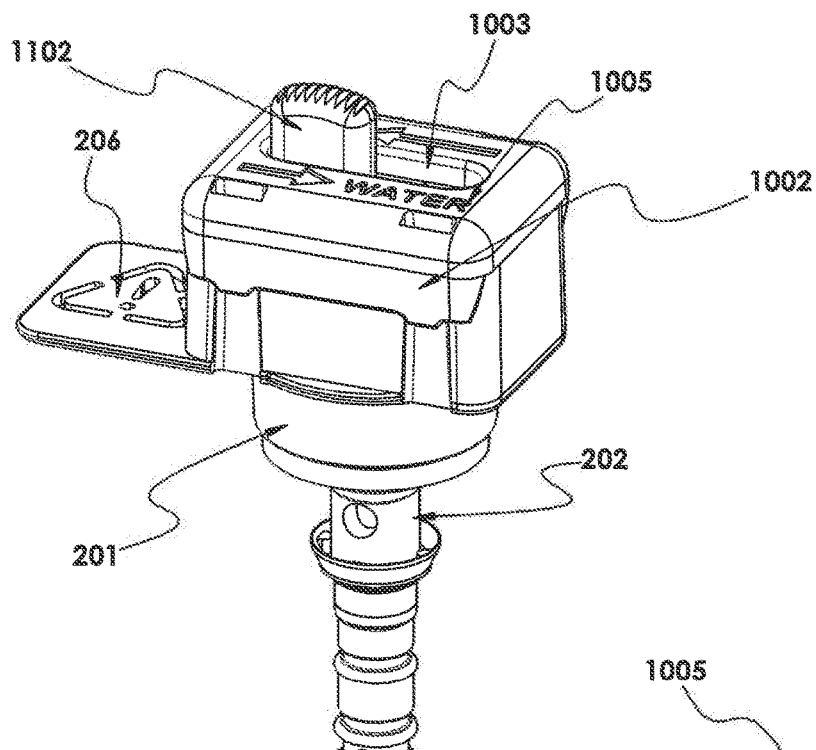
FIG. 11C depicts a sliding switch for an air/water channel pre-cleaning adapter in a first position (at rest) in accordance with an exemplary embodiment.
Figure 11D:
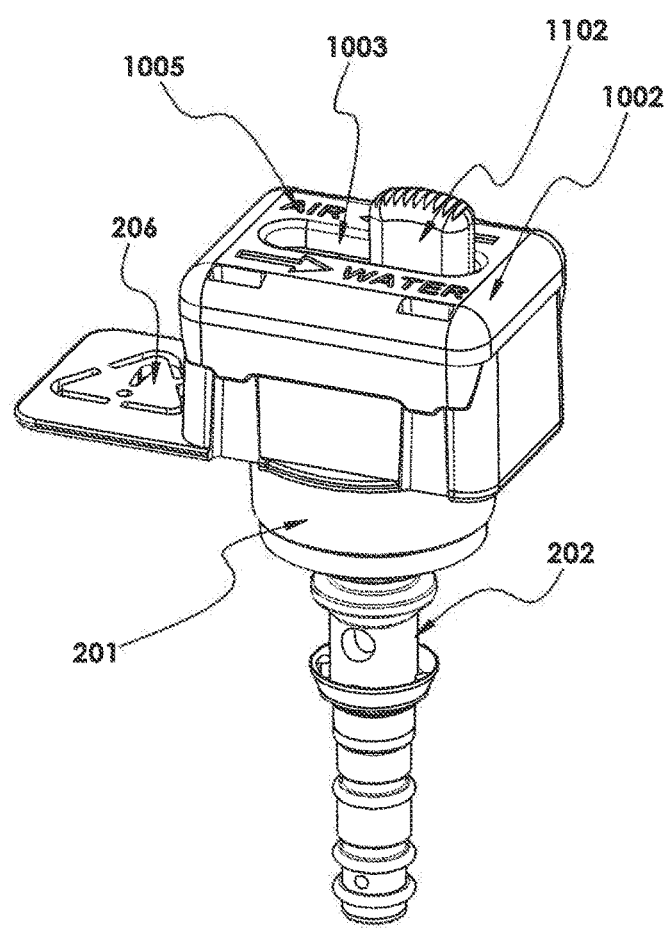
FIG. 11D depicts a sliding switch for an air/water channel pre-cleaning adapter in a second (actuated) position in accordance with an exemplary embodiment.

FIGS. 11A and 11B illustrate additional embodiments of switches that can be used on an air/water pre-cleaning adapter valve in accordance with an exemplary embodiment. FIG. 11A and FIG. 11B illustrates a rocker switch 1101 which operates similarly to the toggle switch illustrated in FIGS. 10A-10F. The rocker switch 1101 moves the valve stem 202 vertically up and down by using the same type of internal cam as used in the toggle switch embodiment. FIG. 11C and FIG. 11D illustrates a slide switch which can be used in place of a toggle switch. By sliding the switch from one side to another, the valve stem moves up and down, that is, it moves up and down in the valve channel in which it is placed. The slide switch 1102 also has "air" and "water" positions. As with the toggle switch, the slide switch eliminates user fatigue because a user is not required to have a finger on the switch during either air or water flow in the pre-cleaning process.

Figure 12A:
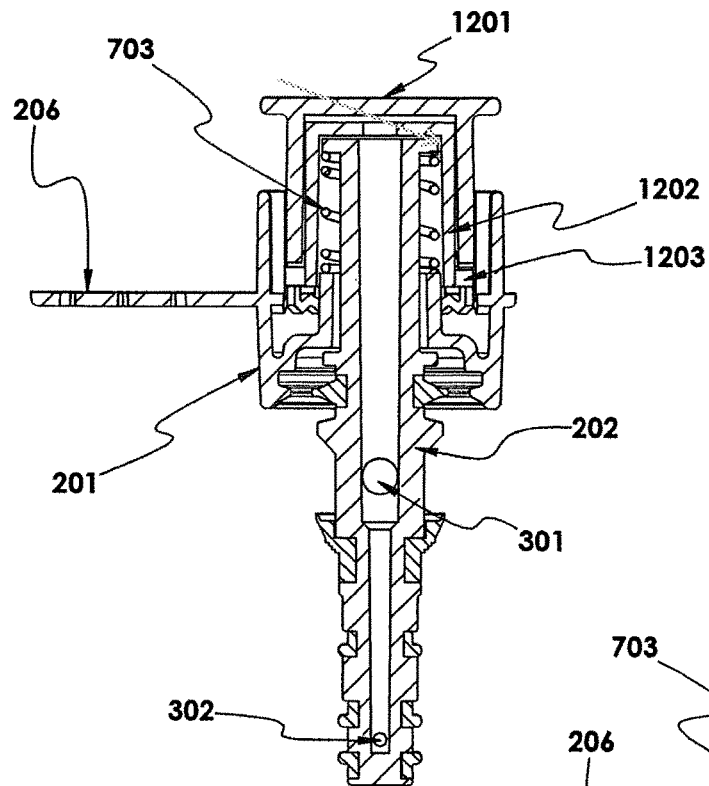
FIG. 12A depicts an extendable/retractable mechanism of an air/water channel pre-cleaning adapter in a first position (at rest), in accordance with an exemplary embodiment. [0058]
Figure 12B:
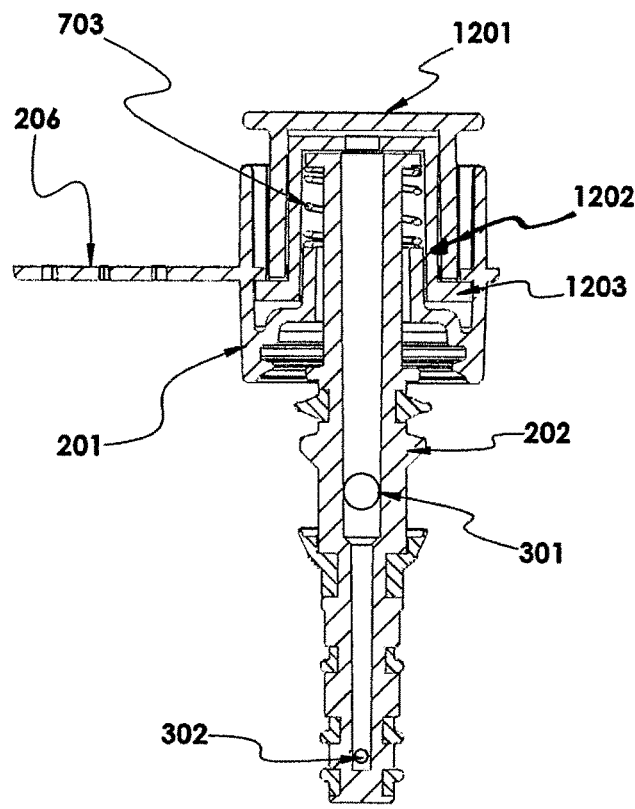
FIG. 12B depicts an extendable/retractable mechanism of an air/water channel pre-cleaning adapter in a second (actuated) position, in accordance with an exemplary embodiment.

FIGS. 12A and 12B illustrate an extendable/retractable ratchet mechanism. In this exemplary embodiment, instead of a cam 1007, a ratchet mechanism is employed to control the proximal/distal position of the valve stem. The button is replaced with an outer plunger 1201 and plunger 1202 which work in tandem to control the position of the valve stem. When the outer plunger 1201 is pressed down, at least one angled protrusion 1203 on the plunger 1202 engages at least one angled surface on the outer plunger 1201. Both plungers move distally in tandem until the angled protrusion 1203 clears grooves in the base 201 and plunger 1202 rotates. When plunger 1202 rotates, the angled protrusion 1203 engages a detent feature in the base 201 which locks the plunger and thereby the valve stem in a distal position relative to the base. When the outer plunger 1201 is pressed again, the plunger 1202 engages the angled protrusion 1203 against the outer plunger 1201 and rotates into grooves that allows the plunger and thereby the valve stem to move back to a proximal location. In this exemplary embodiment, the valve stem provides the same functions whether proximally or distally positioned as described for FIG. 2D and FIG. 2E. As with the toggle switch and rocker switch, the slide switch eliminates user fatigue because a user is not required to have a finger on the switch during either air or water flow in the pre-cleaning process.

The air/water pre-cleaning adapter valve of any of the preceding embodiments can be disposable and can be placed in the air/water channel of an existing endoscope. The air/water channel adapter can be used after an endoscopy procedure is complete to pre-clean the endoscope before it undergoes high level disinfection. The adapter can be attached to the air/water cylinder of a typical endoscope. When the button is in one position, the water from a water container flows through the endoscope's water channel. When the button is in another position, air continuously flows through the air channel. This process flushes debris from the channels.

Accordingly, the various embodiments are not to be limited in scope by the specific embodiments described herein. Further, although some of the embodiments have been described herein in the context of a particular implementation in a particular environment for a particular purpose, those of ordinary skill in the art should recognize that its usefulness is not limited thereto and that the various embodiments can be beneficially implemented in any number of environments for any number of purposes. Accordingly, the claims set forth below should be construed in view of the full breadth and spirit of the embodiments as disclosed herein. While the foregoing description includes many details and specificities, it is to be understood that these have been included for purposes of explanation and are not to be interpreted as limitations of the various embodiments. Many modifications to the embodiments described above can be made without departing from the spirit and scope of this description.

What is claimed is:

1. A device for placement in an air/water cylinder of an endoscope to control the flow of air and water, comprising:
   a base;
   a button comprised of a flexible material and having a half-spherical shape;
   a valve stem, wherein a proximal end of the valve stem extends through the base, and is connected to a distal end of the button;
   a channel positioned longitudinally through the valve stem and having a proximal end and a distal end, the proximal end being sealed by the button;
   a first opening through a wall of the valve stem to the channel at the distal end of the channel; and
   a second opening through the wall of the valve stem to the channel between the distal end of the channel and the proximal end of the valve stem that extends through the base;
   wherein the valve stem is configured to move between a first position and a second position;
   wherein an interior of the button includes a first lock member and the proximal end of the valve stem includes a second lock member configured to operatively interlock with the first lock member; and
   wherein the first lock member is movable with the valve stem.

2. The device of claim 1, wherein in the first position, the button and valve stem are in a proximal position relative to the base.

3. The device of claim 2, wherein in the second position, the button and valve stem are in a distal position relative to the first position.

4. The device of claim 3, wherein in the first position the first and second openings of the stem are each aligned with an air flow channel of an endoscopic device.

5. The device of claim 3, wherein in the second position the first and second openings of the stem are each aligned with a water flow channel of an endoscopic device.

6. The device of claim 1, wherein the button has a dome shape with a depressed central area.

7. The device of claim 1, further comprising a tag attached to the base or other portion of the device.

8. The device of claim 1, wherein the base comprises two or more locking tabs that are configured to connect to an air/water cylinder.

9. The device of claim 1, wherein the device is a single-use device.

10. The device of claim 7, wherein the tag comprises information for a user.

11. The device of claim 7, wherein the tag is molded to the base or other portion of the device.

12. The device of claim 7, wherein the tag is attached to the base or other portion of the device by an elongated element.

13. The device of claim 12, wherein the elongated element is comprised of a string cable or a molded polymer loop.

14. The device of claim 1, further comprising a first seal circumferentially surrounding the valve stem.

15. The device of claim 14, further comprising a second seal and a third seal, wherein the first seal, the second seal, and the third seal are connected by a strip.

16. The device of claim 14, further comprising a second seal and a third seal, wherein the first seal, the second seal, and the third seal are connected to an over-molding positioned circumferentially around the valve stem.

17. The device of claim 1, wherein the button comprises a cylindrical shape with a substantially flat proximal surface and is further comprised of a rigid polymer.

18. The device of claim 1, wherein the button comprises one or more snap features extending in a distal direction within the button, wherein the snap features connect the button to the valve stem.

19. The device of claim 1 further comprising:
   a seal hub arranged at the interior of the button, wherein the seal hub fits into the proximal end of the channel connecting the button to the proximal end of the channel.

20. The device of claim 19, wherein the button is configured to restrict air flowing from the channel through an upper surface of the button.

21. The device of claim 1, wherein the button is configured to restrict air flowing from the channel through an upper surface of the button.

22. The device of claim 1, wherein the second lock member engages the first lock member to directly connect the valve stem to the button.

23. The device of claim 1, wherein the first lock member extends inwardly around an inner circumference of the button.

24. The device of claim 1, wherein the button is depressible and returns to its non-depressed position without a spring.

25. The device of claim 1, wherein the device is springless.

* * * * *